(12) United States Patent
Liu et al.

(10) Patent No.: US 11,396,020 B2
(45) Date of Patent: Jul. 26, 2022

(54) INTEGRATED MICROFLUIDIC DEVICE FOR TARGET AMPLIFICATION AND MICROARRAY DETECTION

(71) Applicants: CapitalBio Corporation, Beijing (CN); Tsinghua University, Beijing (CN)

(72) Inventors: Yan Liu, Beijing (CN); Guohao Zhang, Beijing (CN); Jiang Zhu, Beijing (CN); Zhengde Feng, Beijing (CN); Hongju Guo, Beijing (CN); Jian Gao, Beijing (CN); Wanli Xing, Beijing (CN); Jing Cheng, Beijing (CN)

(73) Assignees: CapitalBio Corporation, Beijing (CN); Tsinghua University, Beijing (CN)

( * ) Notice: Subject to any disclaimer, the term of this patent is extended or adjusted under 35 U.S.C. 154(b) by 428 days.

(21) Appl. No.: 15/128,794

(22) PCT Filed: Mar. 31, 2015

(86) PCT No.: PCT/CN2015/000225
§ 371 (c)(1),
(2) Date: Sep. 23, 2016

(87) PCT Pub. No.: WO2015/149569
PCT Pub. Date: Oct. 8, 2015

(65) Prior Publication Data
US 2017/0095818 A1    Apr. 6, 2017

(30) Foreign Application Priority Data
Mar. 31, 2014   (CN) .................... 201410126515.6

(51) Int. Cl.
*B01L 7/00*     (2006.01)
*B01L 3/00*     (2006.01)
*C12Q 1/6844*   (2018.01)

(52) U.S. Cl.
CPC ............... *B01L 7/52* (2013.01); *B01L 3/5027* (2013.01); *B01L 3/502723* (2013.01);
(Continued)

(58) Field of Classification Search
CPC .... B01L 7/52; B01L 3/5027; B01L 3/502723; B01L 2300/0636; B01L 2200/10;
(Continued)

(56) References Cited

U.S. PATENT DOCUMENTS 8,852,919 B2    10/2014  Zhou
2008/0057572 A1*  3/2008  Petersen .................. B01L 3/502
                                                              435/306.1
(Continued)

FOREIGN PATENT DOCUMENTS

CN    101004423 A    7/2007
CN    102482696 A    5/2012
(Continued)

OTHER PUBLICATIONS

Liu et al. "Review of Temperature Control Technology in Microfluidic PCR Devices", Transducer and Microsystem Technologies, Dec. 31, 2012, vol. 31, 2th, pp. 8-14 (in Chinese).
(Continued)

*Primary Examiner* — Samuel P Siefke
(74) *Attorney, Agent, or Firm* — Rimon, P.C.

(57) ABSTRACT

In one aspect, the present disclosure provides an integrated microfluidic device for nucleic acid amplification and microarray detection. In one aspect, the device comprises: (1) a microchip configured to process reagents, comprising a plurality of reservoirs, channels, valves, and/or fluid interfaces; (2) an amplification chamber for PCR, carried out in a detachable tube assembled on the microchip through a joint; and (3) a microarray chamber comprising a microarray and a reaction chamber. In some embodiments, these fea-
(Continued)

tures are interconnected to allow transportation of reagents for nucleic acid amplification and hybridization detection functions in a closed system. In one aspect, the integrate device herein overcomes the problem of contamination during the amplification and hybridization reactions.

29 Claims, 2 Drawing Sheets

(52) U.S. Cl.
CPC ........ *C12Q 1/6844* (2013.01); *B01L 2200/10* (2013.01); *B01L 2300/048* (2013.01); *B01L 2300/0636* (2013.01); *B01L 2300/0681* (2013.01); *B01L 2300/0867* (2013.01); *B01L 2300/161* (2013.01); *B01L 2400/0487* (2013.01); *B01L 2400/0655* (2013.01)

(58) Field of Classification Search
CPC ....... B01L 2300/048; B01L 2300/0681; B01L 2300/0867; B01L 2300/161; B01L 2400/0487; B01L 2400/0655; C12Q 1/6844
See application file for complete search history.

(56) References Cited

U.S. PATENT DOCUMENTS

| | | |
|---|---|---|
| 2010/0047774 A1 | 2/2010 | Van et al. |
| 2010/0291666 A1 | 11/2010 | Collier et al. |
| 2010/0291668 A1 | 11/2010 | Bertrand et al. |
| 2013/0130267 A1 | 5/2013 | Ludke et al. |
| 2013/0224846 A1 | 8/2013 | Jovanovich et al. |
| 2013/0266948 A1 | 10/2013 | Bird et al. |
| 2014/0065598 A1 | 3/2014 | Zhou et al. |

FOREIGN PATENT DOCUMENTS

| | | |
|---|---|---|
| CN | 103571740 A | 2/2014 |
| CN | 204727866 U | 10/2015 |
| WO | WO-2007/142692 | 12/2007 |
| WO | WO-2013/074885 | 5/2013 |

OTHER PUBLICATIONS

Chen et al. "An integrated, self-contained microfluidic cassette for isolation, amplification, and detection of nucleic acids," Biomed Microdevices, Apr. 17, 2010, pp. 705-719 (in English).

Gu et al. "Microfluidic PCR Biochip and Its Detection Technology," Scientific and Technology Information, Dec. 31, 2012, 20th, pp. 166-167 (in Chinese).

State Intellectual Property Office of the P.R.C, First review notice for Application 2015101456872, dated Aug. 2, 2016, 9 pages.

State Intellectual Property Office of the P.R.C, Notification of Transmittal of the international search report and the written opinion of the international searching authority, or the declaration, dated Jul. 6, 2015, 12 pages.

European Patent Office, Response to Communication pursant to Rules 70(2) and 70a(2) EPC for EP application 157740499, dated May 29, 2018, 17 pages.

Extended European Search Report for EP 15774049.9, dated Nov. 3, 2017, 11 pages.

International Preliminary Report on Patentability for PCT/CN2015/000225, dated Oct. 4, 2016, 5 pages.

International Search Report and Written Opinion for PCT/CN2015/000225, dated Jul. 6, 2015, 7 pages.

Marshall et al., "DNA chips An array of possibilities," Nature Biotechnology (1998) 16:27-31.

Matson et al., "Biopolymer synthesis on polypropylene supports: oligonucleotide arrays," Anal Biochem (1995) 224(1):110-116.

Ramsay, "DNA chips: State-of-the art," Nature Biotechnology (1998) 16:40-44.

Schena et al., "Parallel human genome analysis: microarray-based expression monitoring of 1000 genes," Proc Natl Acad Sci U.S.A (1996) 93(20):10614-10619.

* cited by examiner

INTEGRATED MICROFLUIDIC DEVICE FOR TARGET AMPLIFICATION AND MICROARRAY DETECTION

CROSS REFERENCE TO RELATED APPLICATION

The present application is a U.S. national phase of International Patent Application No. PCT/CN2015/000225, filed Mar. 31, 2015, which claims priority benefit to Chinese Patent Application No. 201410126515.6, filed on Mar. 31, 2014, and published as CN 104946510 A on Sep. 30, 2015, the disclosures of which are incorporated by reference herein in their entireties for all purposes.

TECHNICAL FIELD

In certain aspects, the present disclosure relates to method and apparatus for analysis of biomolecules. In particular aspects, the present disclosure relates to an integrated microfluidic device and methods of using the same, for example, for nucleic acid amplification and detection (e.g., by using a microarray).

BACKGROUND

With the development of molecular diagnostics, nucleic acid analysis is widely employed in areas such as clinical examination, forensic identification, food testing, and academic research. Since the amount of samples subjected to nucleic acid analysis is usually small, and the amount of target molecules in the samples is usually in trace amounts, amplification of a target nucleotide sequence before detection or quantification is often needed. Polymerase chain reaction (PCR) is one of the most prevalent techniques to amplify specific segments of DNA. Once amplified, the DNA may be detected by a variety of techniques, for example, real-time fluorescence detection, gel electrophoresis, capillary electrophoresis, and microarray detection. Microarray technology, which can sensitively and simultaneously measure multiple specific target DNA sequences within a sample, is widely used in diagnostics. Traditional methods of microarray analysis require the following processing steps: nucleic acid amplification, mixing products with hybridization reagents, transferring the mixture to a hybridization chamber, incubating the hybridization reaction, washing, and detection. A variety of commercial instruments, such as microarray hybridizers, clean-up stations, and microarray scanners, are available to perform each individual processing step. However, each individual processing step requires a corresponding device, and manual operation is needed to add and/or transfer reagents between experimental runs and to transfer the sample from one device to another. In the process of transferring amplified products to the microarray chamber, amplified PCR products would be exposed to air, which could easily cause sample cross-contamination. As a result, it is desirable to have an integrate device that possesses both amplification and detection functions, so that carry-over contamination of PCR products can be eliminated or reduced.

One type of devices uses robotic arms to transfer reagents and/or sample between different reaction steps, including nucleic acid amplification, hybridization detection, and purification of nucleic acid before amplification. This type of devices includes, for example, the TruSentry™ System (AkonniBiosystems), and the Prove-it™ StripArray (Mibidiag). However, these devices transfer solutions in an open system, and can cause cross-contamination in the open system.

Several cassettes or microfluidic devices are known for analyzing nucleic acid in a closed environment. These devices integrate a numbers of elements and structures to allow functions for performing amplification and microarray hybridization. For example, US2010/0291668 discloses the iCubate System (Icubate) using a cassette comprising reagent chambers, detection chambers, and cassette pipette for transferring specimens. The pipette could be moved vertically and horizontally within the cassette under the control of an external base unit. US2013/0130267 provides the Unyvero™ Solution (Curetis AG) system using a reaction vessel for performing PCR, above which is provided a specific porous membrane with immobilized microarray probes. Hybridization works by pneumatically controlling liquid to move up and down. U.S. Pat. No. 8,852,919 discloses the Rheonix CARD™ (Rheonix) system which configures membrane-based valves and pneumatic pumps to control reagent transfer between different chambers assembled on a microfluidic device. These devices are small, but they are often in complex geometries and are based on multiple fluid manipulations that are hard to achieve. In addition, complicated fabrication technologies are needed for bonding microfluidic devices to make them withstand high pressure during thermal cycling without causing distortion to fine structures of the devices. Therefore, there is need for an inexpensive microfluidic device that is easy for fluid processing and device fabrication.

SUMMARY

The summary is not intended to be used to limit the scope of the claimed subject matter. Other features, details, utilities, and advantages of the claimed subject matter will be apparent from the detailed description including those aspects disclosed in the accompanying drawings and in the appended claims.

In one aspect, disclosed herein is a microfluidic device for integrated target amplification and detection, comprising a microchip comprising at least one sample reservoir; at least one reagent reservoir; at least one mixing reservoir; and at least one detection chamber, wherein the at least one reagent reservoir is connected to the at least one mixing reservoir, and wherein the at least one mixing reservoir is connected to the at least one detection chamber. In one embodiment, the microchip further comprises at least one connecting structure configured to connect the microchip to at least one amplification chamber. In any of the preceding embodiments, the at least one amplification chamber can be detachable and can be assembled on the microchip through the at least one connecting structure, such as one or more joints on the microchip. In any of the preceding embodiments, the at least one sample reservoir can be connected to the at least one detachable amplification chamber through the at least one connecting structure, such that an amplification reaction can be performed in the at least one detachable amplification chamber. In any of the preceding embodiments, the at least one detachable amplification chamber can be connected to the at least one mixing reservoir through the at least one connecting structure, such that an amplification reaction product from the amplification chamber can be directed to the at least one mixing reservoir, where the amplification product can be mixed with at least one reagent, for example, a reagent for detecting hybridization of the amplification product to a probe in the at least one detection chamber.

In one embodiment, the microfluidic device further comprises at least one amplification chamber, wherein the at least one sample reservoir is connected to the at least one amplification chamber, which is connected to the at least one mixing reservoir. In one embodiment, the at least one amplification chamber is detachable from the microchip. In any of the preceding embodiments, the at least one amplification chamber can be assembled on the microchip through one or more joints. In any of the preceding embodiments, the at least one detection chamber can be detachable from the microchip.

In another aspect, disclosed herein is a microfluidic device for integrated target amplification and detection, comprising a microchip comprising: at least one sample reservoir; at least one amplification chamber; at least one reagent reservoir; at least one mixing reservoir; and at least one detection chamber, wherein the at least one sample reservoir is connected to the at least one amplification chamber, which is connected to the at least one mixing reservoir, wherein the at least one reagent reservoir is connected to the at least one mixing reservoir, and wherein the at least one mixing reservoir is connected to the at least one detection chamber.

In any of the preceding embodiments, the at least one sample reservoir can comprise a reservoir on the microchip for receiving a sample. In any of the preceding embodiments, the at least one sample reservoir can comprise a detachable lid. In any of the preceding embodiments, the detachable lid can comprise an air inlet and a hydrophobic gas-permeable membrane attached to the inside of the lid to cover the air inlet from the inside. In any of the preceding embodiments, the at least one sample reservoir can be connected to the at least one amplification chamber via a first channel in the microchip, a first joint, or a first elastic tube, or any combination thereof. In any of the preceding embodiments, the first channel can comprise a valve that controls the opening or closing of the channel. In any of the preceding embodiments, the first joint can be a screwed nipple, a sleeve joint, or a casting joint. In any of the preceding embodiments, the first elastic tube can comprise silicone, plastic, or rubber. In any of the preceding embodiments, the first elastic tube can be made from a material selected from the group consisting of silicone, plastic, and rubber. In any of the preceding embodiments, the valve can be an elastomeric valve, a phase change valve, or a torque valve.

In one embodiment, the at least one sample reservoir is connected to the first channel in the microchip, the first channel is connected to the first joint, the first joint is connected to the first elastic tube, and the first elastic tube is connected to the at least one amplification chamber.

In any of the preceding embodiments, the at least one amplification chamber can be connected to the at least one mixing reservoir via a second channel in the microchip, a second joint, or a second elastic tube, or any combination thereof. In any of the preceding embodiments, the second channel can comprise a valve that controls the opening or closing of the channel. In any of the preceding embodiments, the second joint can be a screwed nipple, a sleeve joint, or a casting joint. In any of the preceding embodiments, the second elastic tube can comprise silicone, plastic, or rubber. In any of the preceding embodiments, the second elastic tube can be made from a material selected from the group consisting of silicone, plastic, and rubber. In any of the preceding embodiments, the valve can be an elastomeric valve, a phase change valve, or a torque valve.

In one embodiment, the at least one amplification chamber is connected to the second elastic tube, the second elastic tube is connected to the second joint, the second joint is connected to the second channel in the microchip, and the second channel is connected to the at least one mixing reservoir.

In any of the preceding embodiments, the at least one detection chamber can be connected to an inlet channel opening via a first inlet channel in the microchip. In one aspect, the at least one detection chamber is connected to a second inlet channel in the microchip. In one embodiment, the second inlet channel in the microchip is connected to the at least one mixing reservoir via a third channel in the microchip. In one aspect, the third channel comprises a valve that controls the opening or closing of the channel. In any of the preceding embodiments, the valve can be an elastomeric valve, a phase change valve, or a torque valve.

In any of the preceding embodiments, the at least one detection chamber can be connected to an outlet channel opening via an outlet channel in the microchip.

In any of the preceding embodiments, the at least one reagent reservoir can be connected to the at least one mixing reservoir via a fourth channel in the microchip. In one aspect, the fourth channel comprises a valve that controls the opening or closing of the channel. In any of the preceding embodiments, the valve can be an elastomeric valve, a phase change valve, or a torque valve.

In any of the preceding embodiments, the at least one reagent reservoir can comprise a reservoir on the microchip for receiving at least one reagent, and a detachable lid on the reagent reservoir. In one aspect, the detachable lid comprises an air inlet and a hydrophobic air-permeable membrane attached to the inside of the lid to cover the air inlet from the inside. In any of the preceding embodiments, the at least one reagent can be a reagent for nucleic acid hybridization.

In any of the preceding embodiments, the number of the at least one sample reservoir and the number of the at least amplification chamber can be the same or different.

In any of the preceding embodiments, the at least one detection chamber can comprise an array for detection of at least one target molecule in a sample.

In any of the preceding embodiments, the at least one detection chamber can comprise an array for detection of a plurality of target molecules in a sample. In any of the preceding embodiments, the array can be a microarray. In one embodiment, the microarray is a nucleic acid microarray, a protein microarray, a tissue microarray, an antibody microarray, or a combination thereof.

In any of the preceding embodiments, the amplification chamber can comprise a material selected from the group consisting of glass, quartz, rubber, and plastic, or any combination thereof. In any of the preceding embodiments, the microfluidic device can further comprise a supporting platform. In one aspect, the supporting platform comprises a thermal conductive material, such as a metal. In any of the preceding embodiments, the supporting platform can comprise a plate, such as a metal plate. In one embodiment, the plate comprises at least one groove in which the at least one amplification chamber is enclosed or embedded.

In any of the preceding embodiments, the supporting platform can be an integrated part of the microchip or can be detachable from the microchip.

In any of the preceding embodiments, the microfluidic device can further comprise a control subsystem. In one aspect, the control subsystem comprises a fluid control subsystem, an optical subsystem, and/or a thermal control subsystem. In one embodiment, the fluid control subsystem is directly connected to the inlet channel opening, the outlet channel opening, and/or the mixing reservoir opening. In any of the preceding embodiments, the fluid control subsystem can comprise at least one fluid container, at least one pump, and/or at least one valve. In any of the preceding embodiments, the fluid control subsystem can further comprise channel(s) that connects or connect the at least one fluid container, at least one pump, and/or at least one valve. In any of the preceding embodiments, the valve can be an elastomeric valve, a phase change valve, or a torque valve. In one aspect, the at least one fluid container comprises a solution container, a gas container, and/or a waste container. In another aspect, the solution container comprises a washing solution, for example, a solution to wash unbound molecules from a microarray in the detection chamber. In any of the preceding embodiments, the solution container can be connected to the inlet channel opening.

In any of the preceding embodiments, the gas container can comprise a drying air. In any of the preceding embodiments, the gas container can be connected to the inlet channel opening. In one aspect, the waste container is used for collecting waste. In any of the preceding embodiments, the waste container can be connected to the outlet channel opening.

In any of the preceding embodiments, the fluid control system can comprise a pump connected to both the outlet channel opening and the mixing reservoir opening, optionally via a bi-directional valve.

In any of the preceding embodiments, the thermal control subsystem can comprise a heating and/or cooling element for the at least one amplification chamber. In one aspect, the thermal control subsystem further comprises a heating and/or cooling element for the at least one detection chamber.

In any of the preceding embodiments, the optical subsystem can comprise a camera for capturing an image indicating a reaction in the detection chamber, for example, a hybridization reaction on an array in the detection chamber.

In any of the preceding embodiments, the volume of the at least one mixing reservoir can be greater than the total volume of the at least one sample reservoir and the at least one reagent reservoir.

In another aspect, disclosed herein is a kit for integrated target amplification and detection, comprising the microfluidic device of any of the preceding embodiments and optionally one or more reagents for use with the microfluidic device.

In yet another aspect, disclosed herein is a method for integrated target amplification and detection, comprising: adding a sample comprising a target or suspected of comprising a target to the at least one sample reservoir of the microfluidic device of any of the preceding embodiments, and sealing the at least one sample reservoir; adding at least on reagent to the at least one reagent reservoir and sealing the at least one reagent reservoir; operating the microfluidic device to move the sample to the at least one amplification chamber to perform an amplification reaction of the target, if present in the sample; operating the microfluidic device to move a product of the amplification reaction to the at least one mixing reservoir; operating the microfluidic device to move the at least on reagent to the at least one mixing reservoir to mix with the product of the amplification reaction to form a mixture; operating the microfluidic device to move the mixture to the at least one detection chamber to perform a hybridization reaction; and detecting a product of the hybridization reaction, wherein the presence, absence, or amount of the hybridization reaction product indicates the presence, absence, or amount of the target in the sample.

In one aspect, the method further comprising washing the at least one detection chamber with a washing solution. In any of the preceding embodiments, the sample can be a biological sample. In any of the preceding embodiments, the sample can be derived from a tissue or a body fluid, for example, a connective, epithelium, muscle or nerve tissue; a tissue selected from the group consisting of brain, lung, liver, spleen, bone marrow, thymus, heart, lymph, blood, bone, cartilage, pancreas, kidney, gall bladder, stomach, intestine, testis, ovary, uterus, rectum, nervous system, gland, and internal blood vessels; or a body fluid selected from the group consisting of blood, urine, saliva, bone marrow, sperm, an ascitic fluid, and subfractions thereof, e.g., serum or plasma.

In any of the preceding embodiments, the method can analyze the presence, absence, amount, and/or a property of one or a plurality of targets in the sample.

In any of the preceding embodiments, the target can be a polynucleotide, a polypeptide or a small molecule. In any of the preceding embodiments, the polypeptide can be an antibody.

BRIEF DESCRIPTION OF THE DRAWINGS

FIG. 3(a) shows a microarray probe arrangement. FIG. 3(b) shows the fluorescence image of the microarray as arranged in FIG. 3(a) after hybridization of amplified nucleic acid molecules.

DETAILED DESCRIPTION

Figure 1:
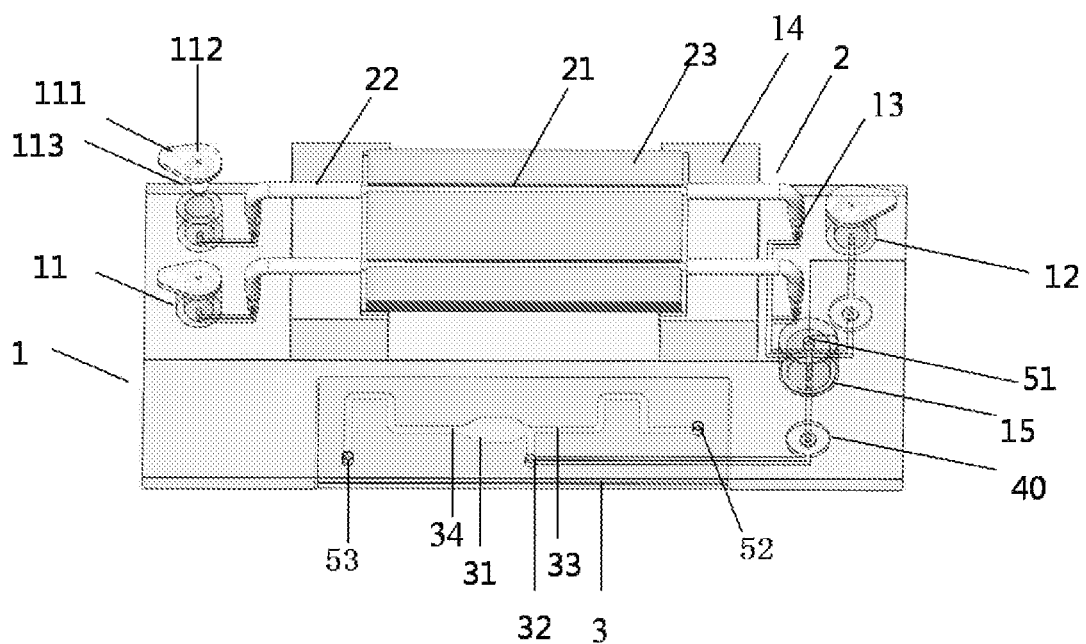
FIG. 1 is a schematic of a microfluidic device according to one aspect of the present disclosure. 1—microfluidic chip, 11—sample reservoir, 111—lid, 112—air inlet, 113—hydrophobic membrane, 12—hybridization reagent reservoir, 13—joint, 14—supporting platform, 15—mixing reservoir, 2—nucleic acid amplification platform, 21—amplification tube, 22—elastic silicone tube, 23—metal plate, 3—microarray platform, 31—microarray chamber (hybridization detection chamber), 32—fluid inlet channel, 33—fluid inlet channel, 34—fluid outlet channel, 40—valve, 51—fluid interface I (mixing reservoir opening), 52—fluid interface II (inlet channel opening), 53—fluid interface III (outlet channel opening).

A detailed description of one or more embodiments of the claimed subject matter is provided below along with accompanying figures that illustrate the principles of the claimed subject matter. The claimed subject matter is described in connection with such embodiments, but is not limited to any particular embodiment. It is to be understood that the claimed subject matter may be embodied in various forms, and encompasses numerous alternatives, modifications and equivalents. Therefore, specific details disclosed herein are not to be interpreted as limiting, but rather as a basis for the claims and as a representative basis for teaching one skilled in the art to employ the claimed subject matter in virtually any appropriately detailed system, structure, or manner. Numerous specific details are set forth in the following description in order to provide a thorough understanding of the present disclosure. These details are provided for the purpose of example and the claimed subject matter may be practiced according to the claims without some or all of these specific details. It is to be understood that other embodiments can be used and structural changes can be made without departing from the scope of the claimed subject matter. It should be understood that the various features and functionality described in one or more of the individual embodiments are not limited in their applicability to the particular embodiment with which they are described. They instead can, be applied, alone or in some combination, to one or more of the other embodiments of the disclosure, whether or not such embodiments are described, and whether or not such features are presented as being a part of a described embodiment. For the purpose of clarity, technical material that is known in the technical fields related to the claimed subject matter has not been described in detail so that the claimed subject matter is not unnecessarily obscured.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

All publications, including patent documents, scientific articles and databases, referred to in this application are incorporated by reference in their entireties for all purposes to the same extent as if each individual publication were individually incorporated by reference. If a definition set forth herein is contrary to or otherwise inconsistent with a definition set forth in the patents, patent applications, published applications or other publications that are herein incorporated by reference, the definition set forth herein prevails over the definition that is incorporated herein by reference. Citation of the publications or documents is not intended as an admission that any of them is pertinent prior art, nor does it constitute any admission as to the contents or date of these publications or documents.

All headings are for the convenience of the reader and should not be used to limit the meaning of the text that follows the heading, unless so specified.

The practice of the provided embodiments will employ, unless otherwise indicated, conventional techniques and descriptions of organic chemistry, polymer technology, molecular biology (including recombinant techniques), cell biology, biochemistry, and sequencing technology, which are within the skill of those who practice in the art. Such conventional techniques include polypeptide and protein synthesis and modification, polynucleotide synthesis and modification, polymer array synthesis, hybridization and ligation of polynucleotides, and detection of hybridization using a label. Specific illustrations of suitable techniques can be had by reference to the examples herein.

However, other equivalent conventional procedures can, of course, also be used. Such conventional techniques and descriptions can be found in standard laboratory manuals such as Green, et al., Eds., *Genome Analysis: A Laboratory Manual Series* (Vols. I-IV) (1999); Weiner, Gabriel, Stephens, Eds., *Genetic Variation: A Laboratory Manual* (2007); Dieffenbach, Dveksler, Eds., *PCR Primer: A Laboratory Manual* (2003); Bowtell and Sambrook, *DNA Microarrays: A Molecular Cloning Manual* (2003); Mount, *Bioinformatics: Sequence and Genome Analysis* (2004); Sambrook and Russell, *Condensed Protocols from Molecular Cloning: A Laboratory Manual* (2006); and Sambrook and Russell, *Molecular Cloning: A Laboratory Manual* (2002) (all from Cold Spring Harbor Laboratory Press); Ausubel et al. eds., *Current Protocols in Molecular Biology* (1987); T. Brown ed., *Essential Molecular Biology* (1991), IRL Press; Goeddel ed., *Gene Expression Technology* (1991), Academic Press; A. Bothwell et al. eds., *Methods for Cloning and Analysis of Eukaryotic Genes* (1990), Bartlett Publ.; M. Kriegler, *Gene Transfer and Expression* (1990), Stockton Press; R. Wu et al. eds., *Recombinant DNA Methodology* (1989), Academic Press; M. McPherson et al., *PCR: A Practical Approach* (1991), IRL Press at Oxford University Press; Stryer, *Biochemistry* (4th Ed.) (1995), W. H. Freeman, New York N.Y.; Gait, *Oligonucleotide Synthesis: A Practical Approach* (2002), IRL Press, London; Nelson and Cox, *Lehninger, Principles of Biochemistry* (2000) 3rd Ed., W. H. Freeman Pub., New York, N.Y.; Berg, et al., *Biochemistry* (2002) 5th Ed., W. H. Freeman Pub., New York, N.Y.; D. Weir & C. Blackwell, eds., *Handbook of Experimental Immunology* (1996), Wiley-Blackwell, all of which are herein incorporated in their entireties by reference for all purposes.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6.

A. Definitions

As used herein and in the appended claims, the singular forms "a," "an," and "the" include plural referents unless the context clearly dictates otherwise. For example, "a" or "an" means "at least one" or "one or more." Thus, reference to "a reagent" refers to one or more reagents, and reference to "the method" includes reference to equivalent steps and methods disclosed herein and/or known to those skilled in the art, and so forth.

As used herein, the term "microfluidic device" generally refers to a device through which materials, particularly fluid borne materials, such as liquids, can be transported, in some embodiments on a micro-scale, and in some embodiments on a nanoscale. Thus, the microfluidic devices described by the presently disclosed subject matter can comprise microscale features, nanoscale features, and combinations thereof.

Accordingly, an exemplary microfluidic device typically comprises structural or functional features dimensioned on the order of a decimeter-scale, centimeter-scale, millimeter-scale or less, which are capable of manipulating a fluid at a flow rate on the order of a µL/min or less. Typically, such features include, but are not limited to channels, fluid reservoirs, reaction chambers, mixing chambers, and separation regions. In some examples, the channels include at least one cross-sectional dimension that is in a range of from about 0.1 µm to about 500 or 5,000 µm. The use of dimensions on this order allows the incorporation of a greater number of channels in a smaller area, and utilizes smaller volumes of fluids.

A microfluidic device can exist alone or can be a part of a microfluidic system which, for example and without limitation, can include: pumps for introducing fluids, e.g., samples, reagents, buffers and the like, into the system and/or through the system; detection equipment or systems; data storage systems; and control systems for controlling fluid transport and/or direction within the device, monitoring and controlling environmental conditions to which fluids in the device are subjected, e.g., temperature, current, and the like.

As used herein, the terms "channel," "micro-channel," "fluidic channel," and "microfluidic channel" are used interchangeably and can mean a recess or cavity formed in a material by imparting a pattern from a patterned substrate into a material or by any suitable material removing technique, or can mean a recess or cavity in combination with any suitable fluid-conducting structure mounted in the recess or cavity, such as a tube, capillary, or the like.

As used herein, the terms "channel," "microchannel," and "flow channel" can include a channel in a microfluidic device in which a material, such as a fluid, e.g., a gas or a liquid, can flow through. More particularly, the terms can include a channel in which a material of interest, e.g., a solvent or a chemical reagent, can flow through. In some embodiments, a material, such as a fluid, e.g., a gas or a liquid, can flow through the channel in such a way to actuate a valve or pump.

As used herein, "chip" refers to a solid substrate with a plurality of one-, two- or three-dimensional micro structures or micro-scale structures on which certain processes, such as physical, chemical, biological, biophysical or biochemical processes, etc., can be carried out. The micro structures or micro-scale structures such as, channels and wells, electrode elements, electromagnetic elements, are incorporated into, fabricated on or otherwise attached to the substrate for facilitating physical, biophysical, biological, biochemical, chemical reactions or processes on the chip. The chip may be thin in one dimension and may have various shapes in other dimensions, for example, a rectangle, a circle, an ellipse, or other irregular shapes. The size of the major surface of chips of the present invention can vary considerably, e.g., from about 1 mm$^2$ to about 0.25 m$^2$. Preferably, the size of the chips is from about 4 mm$^2$ to about 25 cm$^2$ with a characteristic dimension from about 1 mm to about 5 cm. The chip surfaces may be flat, or not flat. The chips with non-flat surfaces may include channels or wells fabricated on the surfaces.

The term "microarray" is used herein to refer to polynucleotide, polypeptide or chemical microarrays. Specific polynucleotides, polypeptides, antibodies, small molecule compounds, peptides, and carbohydrates can be immobilized on solid surfaces to form microarrays.

In one embodiment, the connection between the chambers, tubes, valves, and/or channels of the microfluidic device is substantially air-tight. As used herein, "substantially air-tight" means that gas or air will not leak from the connection in such a way that affects the assay result by more than about 10%, about 5%, about 2%, about 1%, about 0.5%, about 0.1%, about 0.01%, or about 0.001% of the result when the connection is air-tight.

In one embodiment, the amplification tube is rigid or substantially rigid. As used herein, "substantially rigid" means that under a force, the change in a dimension of the amplification tube is less than about 10%, about 5%, about 2%, about 1%, about 0.5%, about 0.1%, about 0.01%, or about 0.001% of the dimension when the force is absent.

As used herein, a "sample" can be a solution, a suspension, liquid, powder, a paste, aqueous, non-aqueous or any combination thereof. A biological sample of the present disclosure encompasses a sample in the form of a solution, a suspension, a liquid, a powder, a paste, an aqueous sample, or a non-aqueous sample. As used herein, a "biological sample" includes any sample obtained from a living or viral (or prion) source or other source of macromolecules and biomolecules, and includes any cell type or tissue of a subject from which nucleic acid, protein and/or other macromolecule can be obtained. The biological sample can be a sample obtained directly from a biological source or a sample that is processed. For example, isolated nucleic acids that are amplified constitute a biological sample. Biological samples include, but are not limited to, body fluids, such as blood, plasma, serum, cerebrospinal fluid, synovial fluid, urine and sweat, tissue and organ samples from animals and plants and processed samples derived therefrom.

An analyte of interest or target that can be detected and/or analyzed using the device disclosed herein can be any biological molecules including but not limited to proteins, nucleic acids, lipids, carbohydrates, ions, or multicomponent complexes containing any of the above. Examples of subcellular analytes of interest include organelles, e.g., mitochondria, Golgi apparatus, endoplasmic reticulum, chloroplasts, endocytic vesicles, exocytic vesicles, vacuoles, lysosomes, etc. Exemplary nucleic acid analyte can include genomic DNA of various conformations (e.g., A-DNA, B-DNA, Z-DNA), mitochondria DNA (mtDNA), mRNA, tRNA, rRNA, hRNA, miRNA, and piRNA.

The term "binding" is used herein to refer to an attractive interaction between two molecules which results in a stable association in which the molecules are in close proximity to each other. Molecular binding can be classified into the following types: non-covalent, reversible covalent and irreversible covalent. Molecules that can participate in molecular binding include polypeptides, polynucleotides, carbohydrates, lipids, and small organic molecules such as pharmaceutical compounds. Polypeptides that form stable complexes with other molecules are often referred to as receptors while their binding partners are called ligands. Polynucleotides can also form stable complex with themselves or others, for example, DNA-protein complex, DNA-DNA complex, DNA-RNA complex.

The term "polypeptide" is used herein to refer to proteins, fragments of proteins, and peptides, whether isolated from natural sources, produced by recombinant techniques, or chemically synthesized. A polypeptide may have one or more modifications, such as a post-translational modification (e.g., glycosylation, etc.) or any other modification (e.g., pegylation, etc.). The polypeptide may contain one or more non-naturally-occurring amino acids (e.g., such as an amino acid with a side chain modification). Polypeptides of the present disclosure may typically comprise at least about 10 amino acids.

The terms "polynucleotide," "oligonucleotide," "nucleic acid" and "nucleic acid molecule" are used interchangeably herein to refer to a polymeric form of nucleotides of any length, and may comprise ribonucleotides, deoxyribonucleotides, analogs thereof, or mixtures thereof. This term refers only to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), including tRNA, rRNA, hRNA, and mRNA, whether spliced or unspliced, any other type of polynucleotide which is an N- or C-glycoside of a purine or pyrimidine base, and other polymers containing normucleotidic backbones, for example, polyamide (e.g., peptide nucleic acid ("PNA")) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. Thus, these terms include, for example, 3'-deoxy-2', 5'-DNA, oligodeoxyribonucleotide N3' to P5' phosphoramidates, 2'-O-alkyl-substituted RNA, hybrids between DNA and RNA or between PNAs and DNA or RNA, and also include known types of modifications, for example, labels, alkylation, "caps," substitution of one or more of the nucleotides with an analog, intemucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including enzymes (e.g. nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, e.g., wherein one or more of the hydroxyl groups are replaced with halogen, aliphatic groups, or are functionalized as ethers, amines, or the like. The term "nucleotidic unit" is intended to encompass nucleosides and nucleotides.

"Nucleic acid probe" and "probe" are used interchangeably and refer to a structure comprising a polynucleotide, as defined above, that contains a nucleic acid sequence that can bind to a corresponding target. The polynucleotide regions of probes may be composed of DNA, and/or RNA, and/or synthetic nucleotide analogs.

As used herein, "complementary or matched" means that two nucleic acid sequences have at least 50% sequence identity. Preferably, the two nucleic acid sequences have at least 60%, 70%, 80%, 90%, 95%, 96%, 97%, 98%, 99% or 100% of sequence identity. "Complementary or matched" also means that two nucleic acid sequences can hybridize under low, middle and/or high stringency condition(s). The percentage of sequence identity or homology is calculated by comparing one to another when aligned to corresponding portions of the reference sequence.

As used herein, "substantially complementary or substantially matched" means that two nucleic acid sequences have at least 90% sequence identity. Preferably, the two nucleic acid sequences have at least 95%, 96%, 97%, 98%, 99% or 100% of sequence identity. Alternatively, "substantially complementary or substantially matched" means that two nucleic acid sequences can hybridize under high stringency condition(s). The percentage of sequence identity or homology is calculated by comparing one to another when aligned to corresponding portions of the reference sequence.

In general, the stability of a hybrid is a function of the ion concentration and temperature. Typically, a hybridization reaction is performed under conditions of lower stringency, followed by washes of varying, but higher, stringency. Moderately stringent hybridization refers to conditions that permit a nucleic acid molecule such as a probe to bind a complementary nucleic acid molecule. The hybridized nucleic acid molecules generally have at least 60% identity, including for example at least any of 70%, 75%, 80%, 85%, 90%, or 95% identity. Moderately stringent conditions are conditions equivalent to hybridization in 50% formamide, 5×Denhardt's solution, 5×SSPE, 0.2% SDS at 42° C., followed by washing in 0.2×SSPE, 0.2% SDS, at 42° C. High stringency conditions can be provided, for example, by hybridization in 50% formamide, 5×Denhardt's solution, 5×SSPE, 0.2% SDS at 42° C., followed by washing in 0.1×SSPE, and 0.1% SDS at 65° C. Low stringency hybridization refers to conditions equivalent to hybridization in 10% formamide, 5×Denhardt's solution, 6×SSPE, 0.2% SDS at 22° C., followed by washing in 1×SSPE, 0.2% SDS, at 37° C. Denhardt's solution contains 1% Ficoll, 1% polyvinylpyrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M EDTA. Other suitable moderate stringency and high stringency hybridization buffers and conditions are well known to those of skill in the art and are described, for example, in Sambrook et al., Molecular Cloning: A Laboratory Manual, 2nd ed., Cold Spring Harbor Press, Plainview, N.Y. (1989); and Ausubel et al., Short Protocols in Molecular Biology, 4th ed., John Wiley & Sons (1999).

Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See M. Kanehisa Nucleic Acids Res. 12:203 (1984).

The terms "homologous," "substantially homologous," and "substantial homology" as used herein denote a sequence of amino acids having at least 50%, 60%, 70%, 80% or 90% identity wherein one sequence is compared to a reference sequence of amino acids. The percentage of sequence identity or homology is calculated by comparing one to another when aligned to corresponding portions of the reference sequence.

A "primer" used herein can be an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Primers usually are extended by a polymerase, for example, a DNA polymerase.

"Multiplexing" or "multiplex assay" herein refers to an assay or other analytical method in which the presence of multiple target molecules can be assayed simultaneously, e.g., by using more than one detection characteristic, e.g., fluorescence characteristic (for example excitation wavelength, emission wavelength, emission intensity, FWHM (full width at half maximum peak height), or fluorescence lifetime).

It is understood that aspects and embodiments of the disclosure herein include "consisting" and/or "consisting essentially of" aspects and embodiments.

Other objects, advantages and features of the present disclosure will become apparent from the following specification taken in conjunction with the accompanying drawings.

B. Integrated Microfluidic Devices

In one aspect, an objective of the present disclosure is to provide an assembled or integrated microfluidic device and a method for nucleic acid amplification and detection (e.g., detection by using a microarray). In one aspect, this is achieved by configuring a microfluidic device with various microfluidic features, including valves, channels, reservoirs, and assay chambers. In some embodiments, the device comprises one or more amplification chambers for PCR, and/or one or more analysis chambers such as a hybridization detection chamber that contains a microarray. In one aspect, some or all of the features in the microfluidic device are interconnected to allow the transportation of one or more reagents for particular applications.

In one aspect, the device herein comprises one or more substrate microchips. In another aspect, the device comprises one or more amplification chambers. In some aspects, the device comprises one or more detection chambers, such as one or more microarray chambers for detecting hybridization of amplified nucleic acids to probes on a microarray. In some embodiments, the device herein comprises one or more substrate microchips, one or more amplification chambers, and/or one or more detection chambers, or any combination thereof. In one aspect, the microchip is configured to process one or more samples using one or more reagents. In particular embodiments, the microchip comprises one or more reservoirs, one or more channels, one or more valves, and/or one or more fluid interfaces or openings. In one aspect, the amplification chamber is configured in a detachable tube, which is assembled on the microchip through one or more joints. In one aspect, this detachable amplification tube reduces the requirement for chip manufacturing technology, compared to configuring the amplification chamber directly on the microchip. In one aspect, the detection chamber comprises one or more microarrays in one or more detection chambers. In one embodiment, the detection chamber is an integrated part of the microchip. In another embodiment, the detection chamber is detachable from the microchip. In another embodiment, the detection chamber is bonded to the microchip, for example, through an adhesive.

In one aspect, the one or more reservoirs on the microchip comprise one or more sample reservoirs, one or more reagent reservoirs (e.g., a hybridization reagent reservoir), and one or more mixing reservoirs. In some embodiments, the sample reservoir and/or reagent reservoir are sealed by a removable lid, which can be opened for adding a sample and/or reagent and closed during assay. In some embodiments, the mixing reservoir is individually in fluid communication with the amplification chamber, the reagent reservoir, and/or the detection chamber through valves and channels. In some aspects, the valves and channels are arranged on the microchip, or buried, enclosed, or embedded in the microchip. In some aspects, an air interface or opening is located at the top of the mixing reservoir to connect with a fluid control subsystem, for example, to a pump in the fluid control subsystem. In some aspects, mixing of amplified PCR product with a hybridization buffer may be achieved by pumping air into the mixing reservoir. In one aspect, the mixture is further transported to the detection chamber, for example, to hybridize with a microarray in the detection chamber. In one aspect, the microchip includes one or more channels configured to transport fluid among the reservoirs and chambers. In some embodiments, the channels comprise valves that control fluid flow in each channel. In one aspect, one or more fluid interfaces or openings on the microchip are configured to communicate with the fluid control subsystem.

In one aspect, the amplification chamber is configured as a cylindrical chamber or tube. In one aspect, the amplification chamber is assembled on the microchip through one or more joints. In one embodiment, the amplification chamber or tube is cylindrical in shape, with an inner diameter of about 0.01 mm-about 10 mm, and an outer diameter of about 0.02 mm-about 20 mm. In particular embodiments, the inner diameter of the amplification chamber or tube is less than about 0.01 mm, between about 0.01 mm and about 0.02 mm, between about 0.02 mm and about 0.04 mm, between about 0.04 mm and about 0.06 mm, between about 0.06 mm and about 0.08 mm, between about 0.08 mm and about 0.10 mm, between about 0.10 mm and about 0.12 mm, between about 0.12 mm and about 0.14 mm, between about 0.14 mm and about 0.16 mm, between about 0.16 mm and about 0.18 mm, between about 0.18 mm and about 0.20 mm, between about 0.20 mm and about 0.22 mm, between about 0.22 mm and about 0.24 mm, between about 0.24 mm and about 0.26 mm, between about 0.26 mm and about 0.28 mm, between about 0.28 mm and about 0.30 mm, between about 0.30 mm and about 0.32 mm, between about 0.32 mm and about 0.34 mm, between about 0.34 mm and about 0.36 mm, between about 0.36 mm and about 0.38 mm, between about 0.38 mm and about 0.40 mm, between about 0.40 mm and about 0.42 mm, between about 0.42 mm and about 0.44 mm, between about 0.44 mm and about 0.46 mm, between about 0.46 mm and about 0.48 mm, between about 0.48 mm and about 0.50 mm, between about 0.50 mm and about 0.52 mm, between about 0.52 mm and about 0.54 mm, between about 0.54 mm and about 0.56 mm, between about 0.56 mm and about 0.58 mm, between about 0.58 mm and about 0.60 mm, between about 0.60 mm and about 0.62 mm, between about 0.62 mm and about 0.64 mm, between about 0.64 mm and about 0.66 mm, between about 0.66 mm and about 0.68 mm, between about 0.68 mm and about 0.70 mm, between about 0.70 mm and about 0.72 mm, between about 0.72 mm and about 0.74 mm, between about 0.74 mm and about 0.76 mm, between about 0.76 mm and about 0.78 mm, between about 0.78 mm and about 0.80 mm, between about 0.80 mm and about 0.82 mm, between about 0.82 mm and about 0.84 mm, between about 0.84 mm and about 0.86 mm, between about 0.86 mm and about 0.88 mm, between about 0.88 mm and about 0.90 mm, between about 0.90 mm and about 0.92 mm, between about 0.92 mm and about 0.94 mm, between about 0.94 mm and about 0.96 mm, between about 0.96 mm and about 0.98 mm, between about 0.98 mm and about 1.00 mm, between about 1.00 mm and about 2.00 mm, between about 2.00 mm and about 3.00 mm, between about 3.00 mm and about 4.00 mm, between about 4.00 mm and about 5.00 mm, between about 5.00 mm and about 6.00 mm, between about 6.00 mm and about 7.00 mm, between about 7.00 mm and about 8.00 mm, between about 8.00 mm and about 9.00 mm, between about 9.00 mm and about 10.00 mm, or more than about 10.00 mm.

In particular embodiments, the outer diameter of the amplification chamber or tube is less than about 0.02 mm, between about 0.02 mm and about 0.04 mm, between about 0.04 mm and about 0.06 mm, between about 0.06 mm and about 0.08 mm, between about 0.08 mm and about 0.10 mm, between about 0.10 mm and about 0.12 mm, between about 0.12 mm and about 0.14 mm, between about 0.14 mm and about 0.16 mm, between about 0.16 mm and about 0.18 mm, between about 0.18 mm and about 0.20 mm, between about 0.20 mm and about 0.22 mm, between about 0.22 mm and about 0.24 mm, between about 0.24 mm and about 0.26 mm, between about 0.26 mm and about 0.28 mm, between about 0.28 mm and about 0.30 mm, between about 0.30 mm and about 0.32 mm, between about 0.32 mm and about 0.34 mm, between about 0.34 mm and about 0.36 mm, between about 0.36 mm and about 0.38 mm, between about 0.38 mm and about 0.40 mm, between about 0.40 mm and about 0.42 mm, between about 0.42 mm and about 0.44 mm, between about 0.44 mm and about 0.46 mm, between about 0.46 mm and about 0.48 mm, between about 0.48 mm and about 0.50 mm, between about 0.50 mm and about 0.52 mm, between about 0.52 mm and about 0.54 mm, between about 0.54 mm and about 0.56 mm, between about 0.56 mm and about 0.58 mm, between about 0.58 mm and about 0.60 mm, between about 0.60 mm and about 0.62 mm, between about 0.62 mm and about 0.64 mm, between about 0.64 mm and about 0.66 mm, between about 0.66 mm and about 0.68 mm, between about 0.68 mm and about 0.70 mm, between about 0.70 mm and about 0.72 mm, between about 0.72 mm and about 0.74 mm, between about 0.74 mm and about 0.76 mm, between about 0.76 mm and about 0.78 mm, between about 0.78 mm and about 0.80 mm, between about 0.80 mm and about 0.82 mm, between about 0.82 mm and about 0.84 mm, between about 0.84 mm and about 0.86 mm, between about 0.86 mm and about 0.88 mm, between about 0.88 mm and about 0.90 mm, between about 0.90 mm and about 0.92 mm, between about 0.92 mm and about 0.94 mm, between about 0.94 mm and about 0.96 mm, between about 0.96 mm and about 0.98 mm, between about 0.98 mm and about 1.00 mm, between about 1.00 mm and about 2.00 mm, between about 2.00 mm and about 3.00 mm, between about 3.00 mm and about 4.00 mm, between about 4.00 mm and about 5.00 mm, between about 5.00 mm and about 6.00 mm, between about 6.00 mm and about 7.00 mm, between about 7.00 mm and about 8.00 mm, between about 8.00 mm and about 9.00 mm, between about 9.00 mm and about 10.00 mm, between about 10.00 mm and about 11.00 mm, between about 11.00 mm and about 12.00 mm, between about 12.00 mm and about 13.00 mm, between about 13.00 mm and about 14.00 mm, between about 14.00 mm and about 15.00 mm, between about 15.00 mm and about 16.00 mm, between about 16.00 mm and about 17.00 mm, between about 17.00 mm and about 18.00 mm, between about 18.00 mm and about 19.00 mm, between about 19.00 mm and about 20.00 mm, or more than about 20.00 mm.

In one aspect, one end of the amplification tube is in fluid communication with the sample reservoir for supplying a liquid sample containing one or more target nucleic acid molecules (such as DNA) to be amplified. In one embodiment, one end of the amplification tube is connected to the sample reservoir via one or more joints and/or one or more channels. In another aspect, the other end of the amplification tube is in fluid communication with the mixing reservoir. In one embodiment, one end of the amplification tube is connected to the mixing reservoir via one or more joints and/or one or more channels.

In any of the preceding embodiments, the detection chamber (such as a microarray chamber) can comprise at least two inlets and/or one outlet. In one aspect, one of the inlets connects to the mixing reservoir via one or more fluid channels. In another aspect, the other inlet is in fluid communication with one or more solution chambers and/or one or more drying air chambers of a fluid control subsystem via one or more fluid interfaces or openings. In some aspects, the outlet is in fluid communication with one or more waste chambers of the fluid control subsystem via one or more fluid interfaces or openings.

In any of the preceding embodiments, the lid for covering the reservoirs can comprise an air inlet on the top and a hydrophobic membrane attached on the inside of the lid to cover the air inlet from the inside. In one aspect, the air inlet keeps the balance of air pressure between the microfluidic device and the environment atmosphere. In another aspect, the hydrophobic membrane prevents at least one product or reagent in the device from getting into the atmosphere. In yet another aspect, the hydrophobic membrane prevents contamination from the environment from getting into the device and interfering with the reaction(s) inside the device.

In any of the preceding embodiments, the mixing reservoir can be configured to possess enough volume, such that during the mixing operation, the mixture remains in the reservoir without overflowing into the one or more subsystems.

In any of the preceding embodiments, the joint described herein can be a screwed nipple, a sleeve joint, or a casting joint.

In any of the preceding embodiments, the amplification tube can be made of glass, quartz, rubber, or plastic, or a combination thereof.

In any of the preceding embodiments, the microfluidic device can comprise a supporting platform. In one aspect, the supporting platform holds the tubes, chambers, reservoirs, and/or channels in position to facilitate interaction between the various components of the device. In one aspect, the supporting platform is equipped with a metal plate, which has one or more grooves. In one aspect, the amplification tube is enclosed or embedded in the groove. When in use, in one aspect, the metal plate closely contacts a heating element in the control subsystem. In one aspect, due to the good thermal conductivity of the metal plate, efficient DNA amplification reaction can be achieved. In one embodiment, the supporting platform is an integrated part of the microfluidic device. In another embodiment, the supporting platform is detachable from the microchip.

In any of the preceding embodiments, the one or more valves can be an elastomeric valve, phase change valve, or torque valve.

In one aspect, when the microfluidic device is in use, the fluid interface or opening on the microfluidic chip communicates with the fluid control subsystem for directing fluid transport in the device. In one aspect, the fluid control subsystem includes one or more fluid containers, pumps, valves, and tubing. In one aspect, the pump is a piston pump or a peristaltic pump. In another aspect, the pump is connected to a stepping motor, which can precisely control fluid in microliter volumes. In one aspect, the valve can be a pinch valve. In some embodiments, the fluid containers comprise one or more solution containers and/or one or more waste containers. In one aspect, the fluid control subsystem connects with one or more fluid interfaces or openings of the microchip through a fluid manifold with O-rings for effective sealing. In one aspect, when the microfluidic device is connected with the fluid control subsystem, a closed environment is formed and avoids contamination in the process of analysis.

Besides the above-mentioned fluid control subsystem, in one aspect, the microfluidic device also works with one or more other control subsystems, including one or more thermal control subsystems to provide heating/cooling to the amplification chamber and/or the microarray detection chamber, and one or more optical systems for capturing images of the microarray. When in use, in one aspect, users only need to add a sample and one or more hybridization reagent to the reservoirs, and then insert the device into an instrument. In one embodiment, the instrument would automatically perform the operation according to a predefined workflow and present the results.

In one aspect, the present microfluidic device realizes the automatic operation for nucleic acid amplification and hybridization detection, and reduces the involvement and/or the requirement for technical expertise of the operators. In one aspect, the whole process is performed in a closed system, avoiding problems of environmental pollution. In another aspect, the nucleic acid amplification is conducted in a detachable amplification tube, reducing the difficulty of chip processing as well as costs associated with chip manufacturing and processing. Also, in one aspect, dynamic hybridization can be applied in the microarray detection chamber by reciprocally moving the sample (e.g., the sample in a mixture with at least one hybridization reagent) back and forth, which promotes the interaction between the microarray probes and the target nucleic acid sequences and reduces the test time.

In one embodiment, an integrated microfluidic device for PCR amplification and hybridization is described herein. In one aspect, the microfluidic device comprises a microchip (e.g., a microfluidic chip), for example, microchip 1 as shown in FIG. 1. In one aspect, the microchip is part of the base of the microfluidic device. In another aspect, the microchip is the base of the microfluidic device. In some embodiments, the microchip comprises an amplification platform and/or a microarray platform. In particular embodiments, the microchip comprises amplification platform 2 and microarray platform 3 as shown in FIG. 1.

In some embodiments, the microchip comprises a sample reservoir and/or a hybridization reagent reservoir. In some embodiments, the microchip comprises a plurality of sample reservoirs and/or at least one hybridization reagent reservoir. In other embodiments, the microchip comprises at least one sample reservoir and/or a plurality of hybridization reagent reservoirs. In still other embodiments, the microchip comprises a plurality of sample reservoirs and/or a plurality of hybridization reagent reservoirs. In a particular embodiment, the microchip comprises two sample reservoirs 11 and a hybridization reagent reservoir 12 as shown in FIG. 1. In one aspect, the sample reservoir is covered by a removable lid. In another aspect, the removable lid comprises an inlet (for example, an air inlet) on the top. In still other aspects, the removable lid comprises a gas permeable hydrophobic membrane affixed to the inside of the lid. In particular embodiments, as shown in FIG. 1, sample reservoir 11 is covered by removable lid 111 with air inlet 112 on the top and gas permeable hydrophobic membrane 113 affixed to the inside of lid. In one aspect, the lid is opened for adding a sample (e.g., an amplification sample) and/or one or more hybridization reagents, and the lid is then fastened for assay.

In one aspect, the sample reservoir is in fluid communication with at least one amplification reaction tube, for example, through a fluid channel or tube and/or a joint machined on the microchip. In particular embodiments, sample reservoir 11 is in fluid communication with amplification reaction tube 21 through fluid channel 22 and joint 13 machined on microchip 1. In one aspect, the amplification tube is gas-tight or substantially gas-tight. In another aspect, the amplification tube is rigid or substantially rigid. In one aspect, the amplification tube comprises silicone or plastic. In one aspect, the amplification tube is a silicone pipe or plastic tube. In a further aspect, the amplification tube is a gas-tight hard silicone pipe or plastic tube. In one aspect, the amplification tube connects to the joint through an elastic tube, for example, a silicone tube. In one embodiment, the inner diameter of the elastic tube in its upstretched state is smaller than the outer diameter of the amplification tube and the outer diameter of the joint, such that when the elastic tube connects the amplification tube to the joint, the elastic tube exerts elastic forces on the amplification tube and the joint to ensure substantially air-tight connection among them. In another aspect, the elastic tube works as a pinch valve, for example, to control fluid flow into and out of the amplification tube. In some embodiments, the elastic tube works in conjunction with one or more valves of the microfluidic device to control fluid flow into and out of the amplification tube. In some embodiments, the elastic tube works as a pinch valve to replace one or more valves of the microfluidic device for controlling fluid flow into and out of the amplification tube.

In specific embodiments, as shown in FIG. 1, amplification tube 21 is a gas-tight hard silicone pipe or plastic tube, which connects to joint 13 through elastic silicone tube 22. The inner diameter of elastic tube 22 in its upstretched state is slightly smaller than the outer diameter of amplification tube 21 and the outer diameter of joint 13, such that elastic tube 22 exerts elastic forces on amplification tube 21 and joint 13 to ensure substantially air-tight connection among them. In some embodiments, elastic silicone tube 22 works as a pinch valve, which in some aspects can replace on-board valve 40 or work in conjunction with one or more valves of the microfluidic device, to control fluid flow into and out of amplification tube 21.

In specific embodiments, the microfluidic device further comprises a plate, for example, a metal plate. In one aspect, the plate comprises a material of good thermal conductivity, for example, a thermal conductivity comparable to or better than that of a metal. In one aspect, the plate comprises one or more groves in which the at least one amplification tube is enclosed or embedded. In another aspect, the microfluidic device further comprises a supporting platform to support the plate and/or the elastic tube. In one aspect, after the microfluidic chip is inserted into an instrument, the plate (e.g., a metal plate) is in close contact with a cooling element and/or a heating element. In one aspect, through the good thermal conductivity of the metal plate, fast thermal exchange between the plate and the amplification tube can be achieved and can be used to rapidly increase or decrease the temperature in the solution or reaction mix inside the amplification tube. In a particular embodiment, as shown in FIG. 1, the microchip comprises supporting platform 14 for supporting metal plate 23 and elastic silicone tube 22. In one aspect, amplification tubes 21 are embedded in grooves of metal plate 23. After inserting the microfluidic chip into an instrument, metal plate 23 closely contacts a cooling element and/or a heating element. In some embodiments, during a PCR reaction, solutions are well confined in the amplification chamber with the corresponding valves closed. After that, valves are opened and the amplified products are directed into one or more mixing reservoirs, for example, mixing reservoir 15 as shown in FIG. 1.

In one aspect, the hybridization reagent reservoir connects with the mixing reservoir. In some embodiments, the hybridization reagent reservoir connects with the mixing reservoir through one or more channels and/or at least one valve. In one aspect, the at least one valve is an elastomeric valve, for example, a pressure-operated elastomeric valve. In one aspect, when there is no external force exerted on the elastic membrane on the valve, the valve is open and the hybridization reagent reservoir and the mixing reservoir are in fluid communication. When external force is applied on the elastic membrane, the membrane is deformed so as to plug the fluid communication. In specific embodiments, as shown in FIG. 1, hybridization reagent reservoir 12 connects with mixing reservoir 15 through a channel and a valve.

In some embodiments, the microfluidic device comprises a hybridization detection chamber. In one aspect, the hybridization detection chamber is provided on the microarray platform. In one aspect, the hybridization detection chamber comprises at least one fluid inlet channel and at least one fluid outlet channel. In one aspect, the hybridization detection chamber comprises a plurality of fluid inlet channels and one fluid outlet channel. In one aspect, the hybridization detection chamber comprises a plurality of fluid inlets channel and a plurality of fluid outlet channels. In specific embodiments, the hybridization detection chamber comprises two fluid inlet channels and one fluid outlet channel. In one aspect, at least one of the fluid inlet channels is connected to an inlet opening through a first channel. In another aspect, at least one of the fluid inlet channels is connected to the mixing reservoir through a second channel. In one aspect, at least one of the fluid outlet channels is connected to an outlet opening through a third channel. In specific embodiments, the microarray platform 3 comprises hybridization detection chamber 31, which comprises two inlet channels 32 and 33 and one outlet channel 34. Inlet channel 33 connects to inlet opening 52 through a first channel inside the microchip, inlet channel 32 connects to mixing reservoir 15 through a second channel inside the microchip, and outlet channel 34 connects to outlet opening 53 through a third channel inside the microchip.

In one embodiment, the mixing reservoir comprises a mixing reservoir opening. In one aspect, the mixing reservoir opening is connected to a pump equipped in a fluid control subsystem. In one aspect, the amplified product and/or the hybridization reagent are sequentially driven, in any suitable order, into the mixing reservoir under the control of the fluid control subsystem comprising at least one pump and/or at least one valve. In one aspect, the amplified product and/or the hybridization reagent are mixed thoroughly by the reciprocating motion of the at least one pump. In one aspect, the mixing reservoir is designed to have a volume that is sufficient to allow bubbles to rise to the top. In one embodiment, the mixing reservoir includes a hydrophobic surface beneath the air interface to prevent solutions from getting into the flow control subsystem. In specific embodiments, as shown in FIG. 1, mixing reservoir 15 comprises mixing reservoir opening 51 on the top, through which mixing reservoir communicates with a pump equipped in a fluid control subsystem. Amplified product and hybridization reagent are sequentially driven into mixing reservoir 15 under the control of the pumps and valves.

In one embodiment, the mixed solution is further delivered to the hybridization detection chamber. In some aspects, the hybridization detection chamber is provided in coordination with at least one heating element, at least one optical element, and/or at least one fluid manifold in the control subsystem. In some aspects, the inlet channel of the hybridization detection chamber is connected with the fluid control subsystem through the inlet channel opening. In some aspects, the outlet channel of the hybridization detection chamber is connected with the fluid control subsystem through the outlet channel opening. In certain embodiments, the fluid control subsystem comprises at least one pump, at least one valve, at least one washing buffer chamber, and/or at least one waste chamber. In one aspect, during hybridization incubation, the specimen or sample is cycled back and forth in the hybridization detection chamber under the control of the reciprocating motion of a pump in the flow control subsystem. In one aspect, this would greatly improve the efficiency of hybridization. In another aspect, at least one heating element is provided to control the reaction temperature during hybridization in the hybridization detection chamber. In another aspect, after the hybridization reaction, the hybridization detection chamber is washed and/or dried under the control of the fluid control subsystem. In specific embodiments as shown in FIG. 1, the mixed solution from mixing reservoir 15 is further delivered to hybridization detection chamber 31, which is provided in coordination with at least one heating element, at least one optical element, and/or at least one fluid manifold in the control subsystem. Inlet channel 33 of the hybridization detection chamber is connected with the fluid control subsystem through fluid inlet channel opening 52. The outlet channel 34 connects with the fluid control subsystem through fluid outlet channel opening 53. During hybridization incubation, in one aspect, the specimen or sample is cycled back and forth in the hybridization detection chamber under the control of the reciprocating motion of a pump, to improve efficiency of hybridization.

In some embodiments, the microchip comprises one or more of the following elements: a center element, a top element, a bottom element, a membrane element, and a joint. In some aspects, the various structures disclosed herein are configured on the center element. In some aspects, the various structures are produced by injection molding techniques and made of a plastic material, such as polycarbonate, polymethylmethacrylate (PMMA), polystyrene, etc. In some aspects, the top and bottom parts are adhesive films and/or plastic plates that are easy to assemble. In some aspects, the top or bottom part may or may not contain at least one of the various structures disclosed herein. In one aspect, the membrane element is seated above the valve structure. In one aspect, the membrane element is made from nitrocellulose, polyvinylidene fluoride (PVDF), polydimethylsiloxane (PDMS), nylon, etc. In certain aspects, the joint described herein is a screwed nipple, a sleeve joint, or a casting joint, etc. In some embodiments, the elements could be bonded together by means of an adhesive or a welding technique, such as laser welding, ultrasound welding, or the like.

Figure 2:
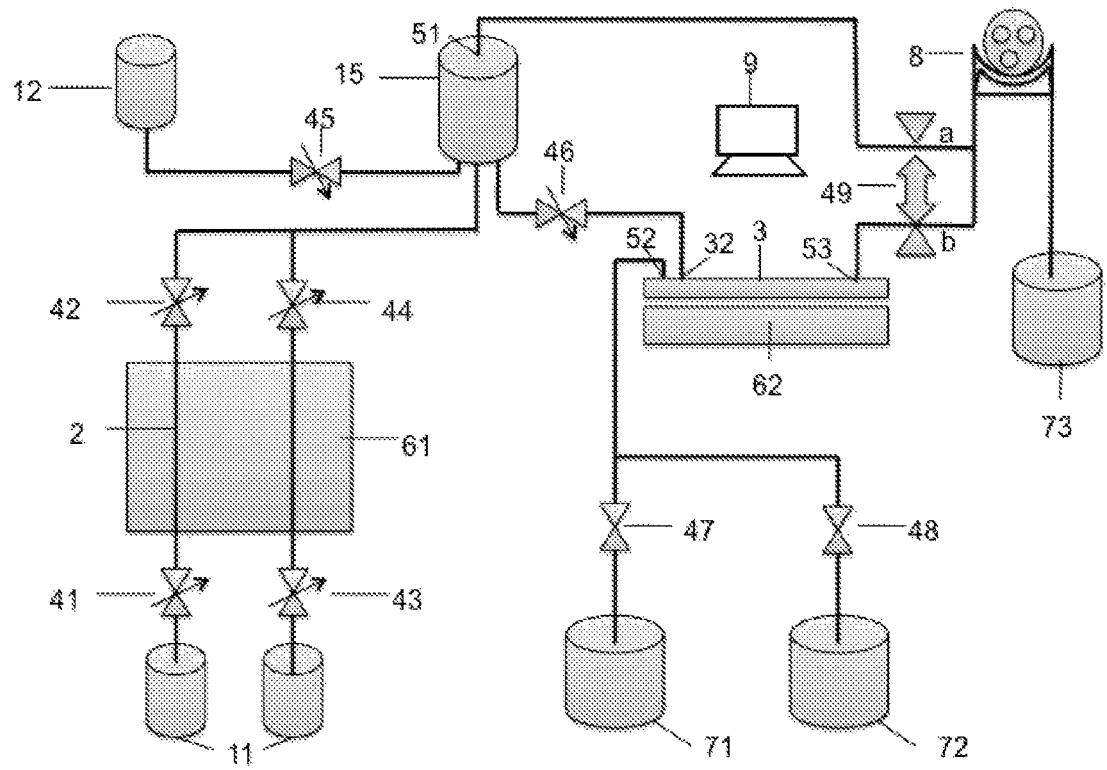
FIG. 2 is a schematic of a control subsystem connected to a microfluidic device according to one aspect of the present disclosure.

In some embodiments, the microfluidic device further comprises a control subsystem. In specific embodiments, a schematic diagram of a control subsystem of the microfluidic device is shown in FIG. 2. In certain aspects, the control subsystem comprises a fluid control subsystem, an optical subsystem, and/or a thermal control subsystem. In one aspect, the fluid control subsystem is directly connected to the fluid interfaces of the microchip (e.g., the inlet channel opening, or the outlet channel opening) through the fluid manifold. In some aspects, the fluid control subsystem comprises at least one fluid container, at least one pump, and/or at least one valve, and tubing that connects the at least one fluid container, at least one pump, and/or at least one valve. In specific embodiments, the at least one fluid container comprises solution/air container 71, solution/air container 72, and waste container 73. In some aspects, container 71 provides solution to wash unbound molecules, and container 72 provides drying air. In some aspects, both container 71 and container 72 are in fluid communication with hybridization detection chamber 31 through tubes and/or channels and fluid interface 52 (inlet channel opening 52). In some aspects, waste container 73 is used for collecting waste. It is in fluid communication with hybridization detection chamber 31 through tubes and/or channels and fluid interface 53 (outlet channel opening 53). In some aspects, pump 8 is equipped at the end of the control system, and connects to both air interface 51 (mixing reservoir opening 51) and fluid interface 53 (outlet channel opening 53) through tubing and bi-directional valve 49. In some aspects, pinch valves 47, 48, and 49 are assembled to control the opening/closing of the tubing. Switchable pressure is applied on valve 41, 42, 43, 44, 45, and/or 46 to cause the deformation of elastic tube 22 or the membrane of valve 40. In some aspects, thermal control elements 61 and 62 are designed for controlling temperature during amplification and hybridization, respectively. For example, thermal control element 61 controls the temperature of amplification platform 2, and thermal control element 62 controls the temperature of hybridization platform 3. In one embodiment, optical system 9 is provided in proximity (for example, above or below) to the hybridization detection chamber to capture an image indicating the hybridization reaction, for example, a microarray result in the hybridization detection chamber.

C. Target Polynucleotide

The target polynucleotide to be detected by using the device herein can be single-stranded, double-stranded, or higher order, and can be linear or circular. Exemplary single-stranded target polynucleotides include mRNA, rRNA, tRNA, hnRNA, microRNA, ssRNA or ssDNA viral genomes and viroids, although these polynucleotides may contain internally complementary sequences and significant secondary structure. Exemplary double-stranded target polynucleotides include genomic DNA, mitochondrial DNA, chloroplast DNA, dsRNA or dsDNA viral genomes, plasmids, phages, shRNA (a small hairpin RNA or short hairpin RNA), and siRNA (small/short interfering RNA). The target polynucleotide can be prepared recombinantly, synthetically, purified from a biological source or a combination thereof. The target polynucleotide may be purified to remove or diminish one or more undesired components of the sample or to concentrate the target polynucleotide prior to amplification. Conversely, where the target polynucleotide is too concentrated for a particular assay, the target polynucleotide may first be diluted.

Following sample collection and optional nucleic acid extraction and purification, the nucleic acid portion of the sample comprising the target polynucleotide can be subjected to one or more preparative treatments. These preparative treatments can include in vitro transcription (IVT), labeling, fragmentation, amplification and other reactions, which can be performed using the device disclosed herein. mRNA can first be treated with reverse transcriptase and a primer, which can be the first primer comprising the target non-complementary region, to create cDNA prior to detection and/or further amplification; this can be done in vitro with extracted or purified mRNA or in situ, e.g., in cells or tissues affixed to a slide. Nucleic acid amplification increases the copy number of sequences of interest and can be used to incorporate a label into an amplification product produced from the target polynucleotide using a labeled primer or labeled nucleotide. A variety of amplification methods are suitable for use, including the polymerase chain reaction method (PCR), transcription mediated amplification (TMA), the ligase chain reaction (LCR), self sustained sequence replication (3SR), nucleic acid sequence-based amplification (NASBA), rolling circle amplification (RCA), loop-mediated isothermal amplification (LAMP), the use of Q Beta replicase, reverse transcription, nick translation, and the like, particularly where a labeled amplification product can be produced and utilized in the methods taught herein.

Any nucleotides may be detected by the present devices and methods. Examples of such nucleotides include AMP, GMP, CMP, UMP, ADP, GDP, CDP, UDP, ATP, GTP, CTP, UTP, dAMP, dGMP, dCMP, dTMP, dADP, dGDP, dCDP, dTDP, dATP, dGTP, dCTP and dTTP.

In some embodiments, the target polynucleotide does not have a label directly incorporated in the sequence. When the target polynucleotide is made with a directly incorporated label or so that a label can be directly bound to the target polynucleotide, this label is one which does not interfere with detection of the capture probe conjugate substrate and/or the report moiety label.

Where the target polynucleotide is single-stranded, the first cycle of amplification forms a primer extension product complementary to the target polynucleotide. If the target polynucleotide is single-stranded RNA, a reverse transcriptase is used in the first amplification to reverse transcribe the RNA to DNA, and additional amplification cycles can be performed to copy the primer extension products. The primers for a PCR must, of course, be designed to hybridize to regions in their corresponding template that will produce an amplifiable segment; thus, each primer must hybridize so that its 3' nucleotide is base-paired with a nucleotide in its corresponding template strand that is located 3' from the 3' nucleotide of the primer used to prime the synthesis of the complementary template strand.

The target polynucleotide may be amplified by contacting one or more strands of the target polynucleotide with a primer and a polymerase having suitable activity to extend the primer and copy the target polynucleotide to produce a full-length complementary polynucleotide or a smaller portion thereof. Any enzyme having a polymerase activity which can copy the target polynucleotide can be used, including DNA polymerases, RNA polymerases, reverse transcriptases, enzymes having more than one type of polymerase activity. The polymerase can be thermolabile or thermostable. Mixtures of enzymes can also be used. Exemplary enzymes include: DNA polymerases such as DNA Polymerase I ("Pol I"), the Klenow fragment of Pol I, T4, T7, Sequenase™ T7, Sequenase™ Version 2.0 T7, Tub, Taq, Tth, Pfx, Pfu, Tsp, Tfl, Tli and Pyrococcus sp GB-D DNA polymerases; RNA polymerases such as E. coli, SP6, T3 and T7 RNA polymerases; and reverse transcriptases such as AMV, M-MuLV, MMLV, RNAse H minus MMLV (SuperScript™), SuperScript™ II, ThermoScript™, HIV-1, and RAV2 reverse transcriptases. All of these enzymes are commercially available. Exemplary polymerases with multiple specificities include RAV2 and Tli (exo-) polymerases. Exemplary thermostable polymerases include Tub, Taq, Tth, Pfx, Pfu, Tsp, Tfl, Tli and Pyrococcus sp. GB-D DNA polymerases.

Suitable reaction conditions are chosen to permit amplification of the target polynucleotide, including pH, buffer, ionic strength, presence and concentration of one or more salts, presence and concentration of reactants and cofactors such as nucleotides and magnesium and/or other metal ions, optional co-solvents, temperature, thermal cycling profile for amplification schemes comprising a polymerase chain reaction, and may depend in part on the polymerase being used as well as the nature of the sample. Co-solvents include formamide (typically at from about 2 to about 10%), glycerol (typically at from about 5 to about 10%), and DMSO (typically at from about 0.9 to about 10%). Techniques may be used in the amplification scheme in order to minimize the production of false positives or artifacts produced during amplification. These include "touchdown" PCR, hot-start techniques, use of nested primers, or designing PCR primers so that they form stem-loop structures in the event of primer-dimer formation and thus are not amplified. Techniques to accelerate PCR can be used, for example centrifugal PCR, which allows for greater convection within the sample, and comprising infrared heating steps for rapid heating and cooling of the sample. One or more cycles of amplification can be performed. An excess of one primer can be used to produce an excess of one primer extension product during PCR; preferably, the primer extension product produced in excess is the amplification product to be detected. A plurality of different primers may be used to amplify different regions of a particular polynucleotide within the sample. Where the amplification reaction comprises multiple cycles of amplification with a polymerase, as in PCR, it is desirable to dissociate the primer extension product(s) formed in a given cycle from their template(s). The reaction conditions are therefore altered between cycles to favor such dissociation; typically this is done by elevating the temperature of the reaction mixture, but other reaction conditions can be altered to favor dissociation, for example lowering the salt concentration and/or raising the pH of the solution in which the double-stranded polynucleotide is dissolved. Although it is preferable to perform the dissociation in the amplification reaction mixture, the polynucleotides may be first isolated using any effective technique and transferred to a different solution for dissociation, then reintroduced into an amplification reaction mixture for additional amplification cycles.

In some aspects, the assay disclosed herein can be multiplexed, e.g., multiple distinct assays can be run simultaneously, by using different pairs of primers directed at different targets, which can be unrelated targets, or different alleles or subgroups of alleles from, or chromosomal rearrangements at, the same locus. This allows the quantitation of the presence of multiple target polynucleotides in a sample (e.g., specific genes in a cDNA library). All that is required is an ability to uniquely identify the different second polynucleotide extension products in such an assay, through either a unique capture sequence or a unique label.

Amplified target polynucleotides may be subjected to post-amplification treatments, for example, by interacting with one or more reagents from the reagent reservoir. In some embodiments, it may be desirable to fragment the amplification products prior to hybridization with a polynucleotide array, in order to provide segments which are more readily accessible and which avoid looping and/or hybridization to multiple capture probes. Fragmentation of the polynucleotides can be carried out by any method producing fragments of a size useful in the assay being performed; suitable physical, chemical and enzymatic methods are known in the art.

Amplified target polynucleotides may also be coupled to the particles, either directly or through modifications to the polynucleotides and/or the particles. In some embodiments, the target polynucleotides are modified, such as biotinylation. In some other embodiments, the particles are modified with a functional group, such as streptavidin, neutravidin, avidin, etc. The target polynucleotides may be coupled to the particles through such modifications and functional groups. For double stranded polynucleotides, following the coupling of the target polynucleotides to the particles, single-stranded target polynucleotides can be prepared by denaturation methods by a chemical reaction, enzyme or heating, or a combination thereof, while coupled to the particles. In some embodiments, the chemical reaction uses urea, formamide, methanol, ethanol, an enzyme, or NaOH. In some embodiments, enzymatic methods include exonuclease and Uracil-N-glycosylase. In some other embodiments, the double-stranded target polynucleotide is heat denatured at an appropriate temperature from about 30° C. to about 95° C.

The method of the present disclosure is suitable for use in a homogeneous multiplex analysis of multiple target polynucleotides in a sample. Multiple target polynucleotides can be generated by amplification of a sample by multiple amplification oligonucleotide primers or sets of primers, each primer or set of primers specific for amplifying a particular polynucleotide target sequence. For example, a sample can be analyzed for the presence of multiple viral polynucleotide target sequences by amplification with primers specific for amplification of each of multiple viral target sequences, including, e.g., human immunodeficiency virus (HIV), hepatitis B virus (HBV), hepatitis C virus (HCV), hepatitis A virus (HAV), parvovirus B19, West Nile Virus, hantavirus, severe acute respiratory syndrome-associated coronavirus (SARS), etc.

The portion of the sample comprising or suspected of comprising the target polynucleotide can be any source of biological material which comprises polynucleotides that can be obtained from a living organism directly or indirectly, including cells, tissue or fluid, and the deposits left by that organism, including viruses, mycoplasma, and fossils. The sample can also comprise a target polynucleotide prepared through synthetic means, in whole or in part. Typically, the sample is obtained as or dispersed in a predominantly aqueous medium. Non-limiting examples of the sample include blood, plasma, urine, semen, milk, sputum, mucus, a buccal swab, a vaginal swab, a rectal swab, an aspirate, a needle biopsy, a section of tissue obtained for example by surgery or autopsy, plasma, serum, spinal fluid, lymph fluid, the external secretions of the skin, respiratory, intestinal, and genitourinary tracts, tears, saliva, tumors, organs, samples of in vitro cell culture constituents (including but not limited to conditioned medium resulting from the growth of cells in cell culture medium, putatively virally infected cells, recombinant cells, and cell components), and a recombinant source, e.g., a library, comprising polynucleotide sequences.

The sample can be a positive control sample which is known to contain the target polynucleotide or a surrogate thereof. A negative control sample can also be used which, although not expected to contain the target polynucleotide, is suspected of containing it, and is tested in order to confirm the lack of contamination by the target polynucleotide of the reagents used in a given assay, as well as to determine whether a given set of assay conditions produces false positives (a positive signal even in the absence of target polynucleotide in the sample).

The sample can be diluted, dissolved, suspended, extracted or otherwise treated to solubilize and/or purify any target polynucleotide present or to render it accessible to reagents which are used in an amplification scheme or to detection reagents. Where the sample contains cells, the cells can be lysed or permeabilized to release the polynucleotides within the cells. Permeabilization buffers can be used to lyse cells which allow further steps to be performed directly after lysis, for example a polymerase chain reaction.

The target polynucleotide may be double stranded or single stranded. In some embodiments, at least a portion of the single-stranded target polynucleotide is completely or substantially complementary to at least a portion of the oligonucleotide probe immobilized on the microarray. In other embodiments, the single-stranded target polynucleotide is completely complementary to the oligonucleotide probe immobilized on the microarray.

The target polynucleotide may be subject to an in vitro manipulation, which may produce single-stranded or double-stranded polynucleotide fragments. The target polynucleotide may be labeled with a luminophore before the in vitro manipulation, during the in vitro manipulation, or after the in vitro manipulation. In one embodiment, physical treatment is employed including laser, ultrasonication, heat, microwave, piezoelectricity, electrophoresis, dielectrophoresis, solid phase adhesion, filtration and fluidic stress. In another embodiment, the in vitro manipulation is selected from the group consisting of enzymatic digestion, isothermal amplification, PCR amplification, reverse-transcription, reverse-transcription PCR amplification, allele-specific PCR (ASPCR), single-base extension (SBE), allele specific primer extension (ASPE), restriction enzyme digestion, strand displacement amplification (SDA), transcription mediated amplification (TMA), ligase chain reaction (LCR), nucleic acid sequence based amplification (NASBA), primer extension, rolling circle amplification (RCA), self sustained sequence replication (3SR), the use of Q Beta replicase, nick translation, and loop-mediated isothermal amplification (LAMP).

For the double-stranded target polynucleotide, they may be denatured by any suitable method, e.g., a chemical reaction, an enzymatic reaction or physical treatment such as heating, or a combination thereof. In some embodiments, the chemical reaction uses urea, formamide, methanol, ethanol, sodium hydroxide, or a combination thereof. In some embodiments, enzymatic methods include exonuclease and Uracil-N-glycosylase treatment. In other embodiments, the double-stranded target polynucleotide is heat denatured at an appropriate temperature from about 30° C. to about 95° C.

D. Microarrays

In a high-throughput manner, microarray technologies enable the evaluation of up to tens of thousands of molecular interactions simultaneously. Microarrays have made significant impact on biology, medicine, drug discovery. DNA microarray-based assays have been widely used, including the applications for gene expression analysis, genotyping for mutations, single nucleotide polymorphisms (SNPs), and short tandem repeats (STRs). And polypeptide and chemical microarrays have emerged as two important tools in the field of proteomics. Chemical microarray, a form of combinatorial libraries, can also be used for lead identification, as well as optimization of these leads. In this era of bioterrorism, the development of a microarray capable of detecting a multitude of biological or chemical agents in the environment will be of great interest to the law enforcement agencies.

According to some embodiments of the present disclosure, assay methods for analysis of molecular interactions are provided. According to some embodiments of the present disclosure, assay methods for multiplexed analysis of target polynucleotides are provided. The target molecules include polynucleotides, polypeptides, antibodies, small molecule compounds, peptides, and carbohydrates.

As those of ordinary skill in the art will recognize, the present disclosure has an enormous number of applications, especially in assays and techniques for pharmaceutical development and diagnostics. The assays may be designed, for example, to detect polynucleotide molecules associated with any of a number of infectious or pathogenic agents including fungi, bacteria, mycoplasma, rickettsia, chlamydia, viruses, and protozoa, or to detect polynucleotide fragments associated with sexually transmitted disease, pulmonary disorders, gastrointestinal disorders, cardiovascular disorders, etc.

A microarray is a multiplex technology widely used in molecular biology and medicine. Microarrays can be fabricated using a variety of technologies, including printing with fine-pointed pins, photolithography using pre-made masks, photolithography using dynamic micromirror devices, ink-jet printing, microcontact printing, or electrochemistry on microelectrode arrays. In standard microarrays, the probe molecules are attached via surface engineering to a solid surface of supporting materials, which include glass, silicon, plastic, hydrogels, agaroses, nitrocellulose and nylon.

The microarray results for the detection of fluorescence-labeled target molecules can be viewed with a suitable method, e.g., by a CCD in bright field (left panel), under a fluorescence microscopy (middle panel), and by a commercial fluorescence microarray scanner with pseudo-color processing (right panel).

For DNA microarray, it comprises an arrayed series of microscopic spots of DNA oligonucleotides, known as probes. This can be a short section of a gene or other DNA element that are used to hybridize a complementary polynucleotide sample (called target) under stringent conditions. Targets in solution are usually detected and quantified by detection of fluorophore-, silver-, or chemiluminescence-labeled targets hybridized on microarray. Since an array can contain several to tens of thousands of probes, a microarray experiment can accomplish many genetic tests in parallel.

The systems described herein may comprise two or more probes that detect the same target polynucleotide. For example, in some embodiments where the system is a microarray, the probes may be present in multiple (such as any of 2, 3, 4, 5, 6, 7, or more) copies on the microarray. In some embodiments, the system comprises different probes that detect the same target polynucleotide. For example, these probes may bind to different (overlapping or non-overlapping) regions of the target polynucleotide.

Any probes that are capable of determining the levels of target polynucleotide can be used. In some embodiments, the probe may be an oligonucleotide. It is understood that, for detection of target polynucleotides, certain sequence variations are acceptable. Thus, the sequence of the oligonucleotides (or their complementary sequences) may be slightly different from those of the target polynucleotides described herein. Such sequence variations are understood by those of ordinary skill in the art to be variations in the sequence that do not significantly affect the ability of the oligonucleotide to determine target polynucleotide levels.

For example, homologs and variants of these oligonucleotide molecules possess a relatively high degree of sequence identity when aligned using standard methods. Oligonucleotide sequences encompassed by the present disclosure have at least 40%, including for example at least about any of 50%, 60%, 70%, 80%, 90%, 95%, 99%, or 100% sequence identity to the sequence of the target polynucleotides described herein. In some embodiments, the oligonucleotide comprises a portion for detecting the target polynucleotides and another portion. Such other portion may be used, for example, for attaching the oligonucleotides to a substrate. In some embodiments, the other portion comprises a non-specific sequence (such as poly-T or poly-dT) for increasing the distance between the complementary sequence portion and the surface of the substrate.

The oligonucleotides for the systems described herein include, for example, DNA, RNA, PNA, ZNA, LNA, combinations thereof, and/or modified forms thereof. They may also include a modified oligonucleotide backbone. In some embodiments, the oligonucleotide comprises at least about any of 5, 6, 7, 8, 9, 10, 12, 13, 14, 15, 16, 17, 18, 19, 20, or more continuous oligonucleotides complementary or identical to all or part of target polynucleotides described herein. A single oligonucleotide may comprise two or more such complementary sequences. In some embodiments, there may be a reactive group (such as an amine) attached to the 5' or 3' end of the oligonucleotide for attaching the oligonucleotide to a substrate.

In some embodiments, the probes are oligonucleotides. Oligonucleotides forming the array may be attached to the substrate by any number of ways including, but not limiting to, (i) in situ synthesis (e.g., high-density oligonucleotide arrays) using photolithographic techniques; (ii) spotting/printing at medium to low density on glass, silicon, nylon or nitrocellulose; (iii) masking; and (iv) dot-blotting on a nylon or nitrocellulose hybridization membrane. Oligonucleotides may also be non-covalently immobilized on the substrate by binding to anchors in a fluid phase such as in microtiter wells, microchannels or capillaries.

Several techniques are well-known in the art for attaching polynucleotides to a solid substrate such as a glass slide. One method is to incorporate modified bases or analogs that contain a moiety that is capable of attachment to a solid substrate, such as an amine group, a derivative of an amine group or another group with a positive charge, into the amplified polynucleotides. The amplified product is then contacted with a solid substrate, such as a glass slide, which may be coated with an aldehyde or another reactive group which can form a covalent link with the reactive group that is on the amplified product and become covalently attached to the glass slide. Microarrays comprising the amplified products can be fabricated using a Biodot (BioDot Inc., Irvine, Calif.) spotting apparatus and aldehyde-coated glass slides (CEL Associates, Houston, Tex.). Amplification products can be spotted onto the aldehyde-coated slides, and processed according to published procedures (Schena et al., Proc. Natl. Acad. Sci. U.S.A. (1995), 93:10614-10619). Arrays can also be printed by robotics onto glass, nylon (Ramsay, G., Nature Biotechnol. (1998), 16:40-44), polypropylene (Matson, et al., Anal Biochem. (1995), 224(1): 110-6), and silicone slides (Marshall and Hodgson, Nature Biotechnol. (1998), 16:27-31). Other approaches to array assembly include fine micropipetting within electric fields (Marshall, and Hodgson, Nature Biotechnol. (1998), 16:27-31), and spotting the polynucleotides directly onto positively coated plates. Methods such as those using amino propyl silicon surface chemistry are also known in the art, as disclosed at cmgm.stanford.edu/pbrown/.

The assays of the present disclosure may be implemented in a multiplex format. Multiplex methods are provided employing 2, 3, 4, 5, 10, 15, 20, 25, 50, 100, 200, 500, 1000 or more different capture probes which can be used simultaneously to assay for amplification products from corresponding different target polynucleotides. In some embodiments, multiplex methods can also be used to assay for polynucleotide target sequences which have not undergone an amplification procedure. Methods amenable to multiplexing, such as those taught herein, allow acquisition of greater amounts of information from smaller specimens. The need for smaller specimens increases the ability of an investigator to obtain samples from a larger number of individuals in a population to validate a new assay or simply to acquire data, as less invasive techniques are needed.

Where different substrates are included in a multiplex assay as part of the capture probe conjugates, the different substrates can be encoded so that they can be distinguished. Any encoding scheme can be used; conveniently, the encoding scheme can employ one or more different fluorophores, which can be fluorescent semiconductor nanocrystals. High density spectral coding schemes can be used.

One or more different populations of spectrally encoded capture probe conjugates can be created, each population comprising one or more different capture probes attached to a substrate comprising a known or determinable spectral code comprising one or more semiconductor nanocrystals or fluorescent nanoparticle. Different populations of the conjugates, and thus different assays, can be blended together, and the assay can be performed in the presence of the blended populations. The individual conjugates are scanned for their spectral properties, which allows the spectral code to be decoded and thus identifies the substrate, and therefore the capture probe(s) to which it is attached. Because of the large number of different semiconductor nanocrystals and fluorescent nanoparticles and combinations thereof which can be distinguished, large numbers of different capture probes and amplification products can be simultaneously interrogated.

In one embodiment, the microarray comprises at least two probe molecules. In another embodiment, the microarray comprises multiple oligonucleotide probes. In yet another embodiment, the probe molecule is selected from the group consisting of a polynucleotide, a polypeptide, an antibody, a small molecule compound, a peptide and a carbohydrate.

In one embodiment, the single-stranded target polynucleotide obtained may comprise an artificially designed and optimized polynucleotide sequence such as a Tag sequence. In yet another embodiment, the microarray comprises a universal Tag array. In still another embodiment, the Tag sequences are complementary or substantially complementary to the oligonucleotide probes on the universal Tag array.

The $T_m$ difference between different Tag sequences can be set at any suitable range, e.g., equals to or is less than about 5° C. In some embodiments, the Tag sequences have no cross-hybridization among themselves. In some other embodiments, the Tag sequences have low homology to the genomic DNA of the species. In preferred embodiments, the Tag sequences have no hair-pin structures. In one embodiment, the Tag sequence is a single stranded oligonucleotide or modified analog. In another embodiment, the Tag sequence is a locked nucleic acid (LNA), a zip nucleic acid (ZNA) or a peptide nucleic acid (PNA). In yet another embodiment, the Tag sequence is introduced to the target polynucleotide during an in vitro manipulation.

E. Use of the Microfluidic Chip

The present microfluidic chip can be used in any suitable assay to improve assay precision, reproducibility, and/or sensitivity, particularly for the assays involving small reaction volumes. For instance, the microfluidic chip can be used in assaying the interaction between various moieties, e.g., nucleic acids, immunoreactions involving proteins, interactions between a protein and a nucleic acid, a ligand-receptor interaction, and small molecule and protein or nucleic acid interactions, etc.

The present microfluidic chip can be used to assay any analyte, e.g., a cell, a cellular organelle, a virus, a molecule and an aggregate or complex thereof. Exemplary cells include animal cells, plant cells, fungus cells, bacterium cells, recombinant cells and cultured cells. Animal, plant, fungus, bacterium cells can be derived from any genus or subgenus of the Animalia, Plantae, fungus or bacterium kingdom. Cells derived from any genus or subgenus of ciliates, cellular slime molds, flagellates and microsporidia can also be assayed by the present methods. Cells derived from birds such as chickens, vertebrates such as fish and mammals such as mice, rats, rabbits, cats, dogs, pigs, cows, ox, sheep, goats, horses, monkeys and other non-human primates, and humans can be assayed by the present methods.

For animal cells, cells derived from a particular tissue or organ can be assayed. For example, connective, epithelium, muscle or nerve tissue cells can be assayed. Similarly, cells derived from an internal animal organ such as brain, lung, liver, spleen, bone marrow, thymus, heart, lymph, blood, bone, cartilage, pancreas, kidney, gall bladder, stomach, intestine, testis, ovary, uterus, rectum, nervous system, gland, internal blood vessels, etc. can be assayed. Further, cells derived from any plants, fungi such as yeasts, bacteria such as eubacteria or archaeabacteria can be assayed. Recombinant cells derived from any eucaryotic or prokaryotic sources such as animal, plant, fungus or bacterium cells can also be assayed. Body fluid such as blood, urine, saliva, bone marrow, sperm or other ascitic fluids, and subfractions thereof, e.g., serum or plasma, can also be assayed.

Exemplary cellular organelles include nuclei, mitochondria, chloroplasts, ribosomes, ERs, Golgi apparatuses, lysosomes, proteasomes, secretory vesicles, vacuoles and microsomes. Exemplary molecules include inorganic molecules, organic molecules and a complex thereof. Exemplary organic molecules include amino acids, peptides, proteins, nucleosides, nucleotides, oligonucleotides, nucleic acids, vitamins, monosaccharides, oligosaccharides, carbohydrates, lipids and a complex thereof.

Any nucleosides can be assayed by the present microfluidic chip. Examples of such nucleosides include adenosine, guanosine, cytidine, thymidine and uridine. Any nucleotides can be assayed according to the present disclosure. Examples of such nucleotides include AMP, GMP, CMP, UMP, ADP, GDP, CDP, UDP, ATP, GTP, CTP, UTP, dAMP, dGMP, dCMP, dTMP, dADP, dGDP, dCDP, dTDP, dATP, dGTP, dCTP and dTTP. Any nucleic acids, including single-, double and triple-stranded nucleic acids, can be assayed by the present microfluidic chip. Examples of such nucleic acids include DNA, such as A-, B- or Z-form DNA, and RNA such as mRNA, miRNA, piRNA, tRNA and rRNA.

The present microfluidic chip can be used to assay any sample. For example, the present method can be used to assay a mammalian sample. Exemplary mammals include bovines, goats, sheep, equines, rabbits, guinea pigs, murine, humans, felines, monkeys, dogs and porcines. The present microfluidic chip can also be used to assay a clinical sample. Exemplary clinical samples include serum, plasma, whole blood, sputum, cerebral spinal fluid, amniotic fluid, urine, gastrointestinal contents, hair, saliva, sweat, gum scrapings and tissue from biopsies. Preferably, the present microfluidic chip is used to assay a human clinical sample.

Any suitable reagents can be used in an assay according to the present disclosure. In one aspect, the reagents used in the present disclosure bind or interact specifically with an analyte in a sample. Exemplary reagents include cells, cellular organelles, viruses, molecules and an aggregate or complex thereof. In one aspect, the reagent is an antibody, or a nucleic acid.

The present microfluidic chip can be used in any suitable assay format, for example, in a direct assay format, a sandwich assay format or a competition assay format. In one embodiment, a different plurality of reagents are used to assay a single analyte. In another embodiment, a different plurality of reagents are used to assay a different plurality of analytes. In still another embodiment, a plurality of reagents are attached to the inner surface of the amplification chamber or hybridization chamber, and is used, for example, to assay one or more analytes in one or more samples.

The present microfluidic chip can be used to detect any interaction(s) among moieties selected from the group consisting of a cell, a cellular organelle, a virus, a molecule and an aggregate or complex thereof. For example, interactions between or among macromolecules, such as DNA-DNA, DNA-RNA, RNA-RNA, DNA-protein, RNA-protein and protein-protein, etc., interactions can be analyzed. In other embodiments, macromolecule-small molecule or small molecule-small molecule interactions are detected or analyze using the present microfluidic chip. More complex interactions including interactions among more than two moieties can also be detected and/or analyzed according to the present disclosure. When DNA-DNA, DNA-RNA, RNA-RNA interactions are to be detected, the contacting, i.e., hybridizing, step, can be conducted under suitable condition, e.g., under low, middle or high stringency, after samples or reagents are delivered to the reaction volumes according to the present disclosure.

The interaction between a test moiety and a plurality of target moieties can be detected by any suitable methods, and the present microfluidic chip can be made to suit the particular detection method. For example, the test moiety and/or target moieties can be labeled to facilitate detection. Any suitable label can be used. Exemplary labels include a radioactive, a fluorescent, a chemical, an enzymatic, a luminescent and a FRET (fluorescence resonance energy transfer) label. The luminescent label can be a chemiluminescent label or a bioluminescent label. The labels can be attached or conjugated, directly or indirectly, to the test moiety alone, the target moiety alone, or on both. The read-out can be a positive or a negative signal. Any suitable assay formats, including sandwich or competitive formats, can be used. Any of the samples or reagents, including the labels, primers or dNTPs of a PCR reaction, or an enzyme, can be delivered using the present microfluidic chip.

In one embodiment, the present microfluidic chip is used to detect interaction between or among a test moiety and a plurality of genes, gene fragments or their encoded products. For instance, the plurality of target genes, gene fragments or their encoded products are involved in a biological pathway, belong to a group of proteins with identical or similar biological function, expressed in a stage of cell cycle, expressed in a cell type, expressed in a tissue type, expressed in an organ type, expressed in a developmental stage, proteins whose expression and/or activity is altered in a disease or disorder type or stage, or proteins whose expression and/or activity is altered by drug or other treatments.

The present microfluidic chip can be used in detecting interaction between or among a single test moiety or substance and a plurality of target moieties. Preferably, the present methods are used in high-throughput mode, e.g., in detecting a plurality of target moieties, and/or interaction between or among a plurality of test moieties or substances. The interaction between a plurality of test moieties or substances and a plurality of target moieties can be detected simultaneously or sequentially.

Microfluidic chips of the present the present disclosure can be used in a variety of applications and reactions, including but not limited to, nucleic acid amplification reactions, biochemical reactions, immune reactions, and so on.

The present microfluidic chips and methods can be used to detect a number of infectious diseases or infection states in a subject. Pathogenic viruses include, but are not limited to, Retroviridae (e.g., human immunodeficiency viruses, such as HIV-1 (also referred to as HTLV-III, LAV or HTLV-III/LAV, or HIV-III); and other isolates, such as HIV-LP; Picornaviridae (e.g., polio viruses, hepatitis A virus; enteroviruses, human coxsackie viruses, rhinoviruses, echoviruses); Caliciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever viruses); Reoviridae (e.g., reoviruses, orbiviurses and rotaviruses); Bimaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes viruses); Poxyiridae (variola viruses, vaccinia viruses, pox viruses); and Iridoviridae (e.g., African swine fever virus); Hepatitis C virus; and unclassified viruses (e.g., the agent of delta hepatitis (thought to be a defective satellite of hepatitis B virus); Norwalk and related viruses, and astroviruses).

Pathogenic bacteria include, but are not limited to, *Helicobacter pyloris, Borelia burgdorferi, Legionella pneumophila, Mycobacteria* sps (e.g. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyrogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, Corynebacterium diphtheriae, Corynebacterium* sp., *Erysipelothrix rhusiopathiae, Clostridium perfringens, Clostridium tetani, Enterobacter aerogenes, Klebsiella pneumoniae, Pasturella multocida, Bacteroides* sp., *Fusobacterium nucleatum*, pathogenic strains of *Escherichia coli, Streptobacillus moniliformis, Treponema pallidium, Treponema pertenue, Leptospira*, and *Actinomyces israelii*.

Infectious fungi include, but are not limited to, *Cryptococcus neoformans, Histoplasma capsulatum, Coccidioides immitis, Blastomyces dermatitidis, Chlamydia trachomatis, Candida albicans*.

Infectious protozoa include, but are not limited to, *Plasmodium* spp., e.g., *Plasmodium falciparum*; Trypanosomes, e.g., *Trypanosoma cruzi*; and *Toxoplasma gondii*.

It is to be understood that the present microfluidic chips are suitable for detection of the above infectious agents by detecting their genetic material, for example, by PCR of specific nucleic acid sequences that are indicative of the infectious agents, by detecting proteins, lipids, or polysaccharides that are indicative of the infectious agents, and/or by detecting host responses to the infectious agents (e.g., host antibodies to the infectious agents).

The following embodiments are intended to further describe and illustrate various aspects of the present disclosure, but not to limit, the scope of the present disclosure in any manner, shape, or form, either explicitly or implicitly.

Embodiment 1: An assembled microfluidic device for nucleic acid amplification and microarray detection, characterized in that the device comprises a microchip (e.g., a substrate microchip), wherein:

the microchip comprises at least one sample reservoir, at least one hybridization reagent reservoir, and at least one mixing reservoir, and the at least one sample reservoir and the at least one hybridization reagent reservoir are each sealed by a removable lid;

the microfluidic device comprises at least one amplification chamber on the microchip, and comprises the same number of amplification chambers as the sample reservoirs;

the at least one amplification chamber is in fluid communication with a first channel in the microchip via a first joint, and the first channel is in fluid communication with the at least one sample reservoir;

the at least one amplification chamber is in fluid communication with a second channel in the microchip via a second joint, the second channel is in fluid communication with the at least one mixing reservoir, and the at least one mixing reservoir comprises a mixing reservoir opening;

the microchip comprises at least one hybridization detection chamber comprising at least two inlet channels and at least one outlet channel;

one of the at least two inlet channels is in fluid communication with an inlet channel opening on the microchip, another one of the at least two inlet channels is in fluid communication with the mixing reservoir via a third channel in the microchip, and the at least one outlet channel is in fluid communication with an outlet channel opening on the microchip;

the at least one hybridization reagent reservoir is in fluid communication with the mixing reservoir via a fourth channel in the microchip; and there is at least one valve on the first, second, third, and fourth channels, and the at least one valve controls the opening or closing of the corresponding channel.

Embodiment 2: The microfluidic device of embodiment 1, wherein the lid for covering the reservoirs comprises an air inlet on the top, and a hydrophobic air-permeable membrane attached to the inside of the lid and cover the of air inlet from the inside.

Embodiment 3: The microfluidic device of embodiment 1 or 2, wherein the joint is a screwed nipple, a sleeve joint, or a casting joint.

Embodiment 4: The microfluidic device of any of embodiments 1-3, wherein the amplification chamber comprises a material selected from the group consisting of glass, quartz, rubber, and plastic.

Embodiment 5: The microfluidic device of any of embodiments 1-4, wherein the amplification chamber is connected to the joint via an elastic tube, wherein the elastic tube optionally comprises a material selected from the group consisting of silicon, plastic, and rubber.

Embodiment 6: The microfluidic device of any of embodiments 1-5, wherein the microfluidic device comprises a supporting platform to hold the tubes and channels in a position to facilitate interaction between various components of subsystems, wherein the supporting platform comprises a metal plate comprising at least one groove in which the amplification chamber is enclosed or embedded, and wherein the supporting platform is an integrated part of the microfluidic device or is detachable from the microchip.

Embodiment 7: The microfluidic device of any of embodiments 1-6, wherein the volume of the at least one mixing reservoir is greater than the total volume of the at least one sample reservoir and the at least one hybridization reagent reservoir.

Embodiment 8: The microfluidic device of any of embodiments 1-7, wherein the valve is an elastomeric valve, a phase change valve or a torque valve.

Example 1

Detection of Genetic Mutations Associated with Hearing Loss Using the Microfluidic Device In this example, genetic mutations associated with hearing loss were analyzed and detected using an exemplary microfluidic device and control subsystem disclosed herein.

Genetic hearing loss mutation detection kit (microarray method) (CapitalBio Corporation, Beijing, China) was used for the analysis. Dried blood on filter paper was collected as the test sample. Extraction of blood sample was processed according to kit instructions. Extracted DNA was mixed with PCR reagents in the kit. The PCR mixture was added to the sample reservoir using a pipette. The hybridization reagent was also added to the reagent reservoir. All the sample reservoirs and hybridization reservoir were covered by a lid during the assay. Then the device was initialized and placed into the instrument. The instrument automatically completed the remaining operation.

1. System Initialization

1) Washing solution preparation: solution 1 (0.3×SSC and 0.1% SDS) was loaded into container 71 as shown in FIG. 2, solution 2 (0.06×SSC) was loaded into container 72.

2) Fluid prefilling: pinch valve 47 was opened and bi-direction valve 49 was switched to close the "a" side and open the "b" side. Solution container 71 was in fluid communication with waste container 73 through tubes of the fluid control system and an inner flow path of the subsystem (inner flow path not shown). The peristaltic pump moved in the counter-clockwise direction, and tubes of the fluid path were filled with liquid. Pinch valve 47 was then closed, and pinch valve 48 was opened. Pinch valve 49 was then switched to the other side ("a" side open and "b" side closed), and the other branch of the tubes of the fluid path were filled with liquid.

2. Loading the Microfluidic Device

The microfluidic device with the sample and reagents loaded was then inserted into an instrument containing the control systems. In some aspects, an optical sensor or magnetic sensor was used to validate the position of the device. At the same time, a spring or a slot design was used to ensure the microfluidic device closely contact the heating elements. Also the fluid interface on the microchip was closely connected with the fluid manifold in the fluid control subsystem.

3. Amplification

All valves were closed. The bi-direction valve 49 was switched to open the "a" side and close the "b" side. Valves 41 and 42 were then opened. The PCR sample was pumped into the amplification tube. Then valves 41 and 42 were closed. Similarly, by controlling valves 43 and 44, another PCR sample was directed to the corresponding amplification tube. PCR was carried out according to a preset thermal cycling program.

4. Mixing

Pinch valves 41 and 42 were opened, and amplified products were pumped to the mixing tank. Valves 41 and 42 were then closed. The same operation was performed on the other amplification tube controlled by valves 43 and 44. After that, valve 45 was opened to draw hybridization reagents to the mixing reservoir. The peristaltic pump was operated to move back and forth to generate reciprocating motion of the mixture inside the mixing reservoir. Intensive mixing of PCR product was obtained to prepare for hybridization.

5. Hybridization

Valve 46 was opened. The bi-direction valve 49 was switched to open the "b" side. The mixture of PCR product and hybridization reagent was directed into microarray chamber 31. The microarray chamber was heated to 60° C. by setting the temperature control elements. Again, the peristaltic pump was operated to move back and forth to generate reciprocating motion of the mixture inside the microarray chamber. This dynamic hybridization procedure greatly improved the efficiency of target nucleic acid sequences binding to the probes immobilized on the chamber.

6. Cleaning

After hybridization incubation, the temperature of the microarray chamber was decreased to 25° C. Pinch valve 47 was opened. Solution was pumped from container 71 to the microarray chamber for washing away nucleic acid unbound to the probes. The liquid containing the unbound nucleic acid was further directed into the waste chamber. Similarly, the hybridization detection chamber (the microarray chamber) was cleaned by the solution in container 72.

7. Detection

Through the LED light source and the CCD camera, images or videos of the microarray were obtained.

Figures 3A, 3B:
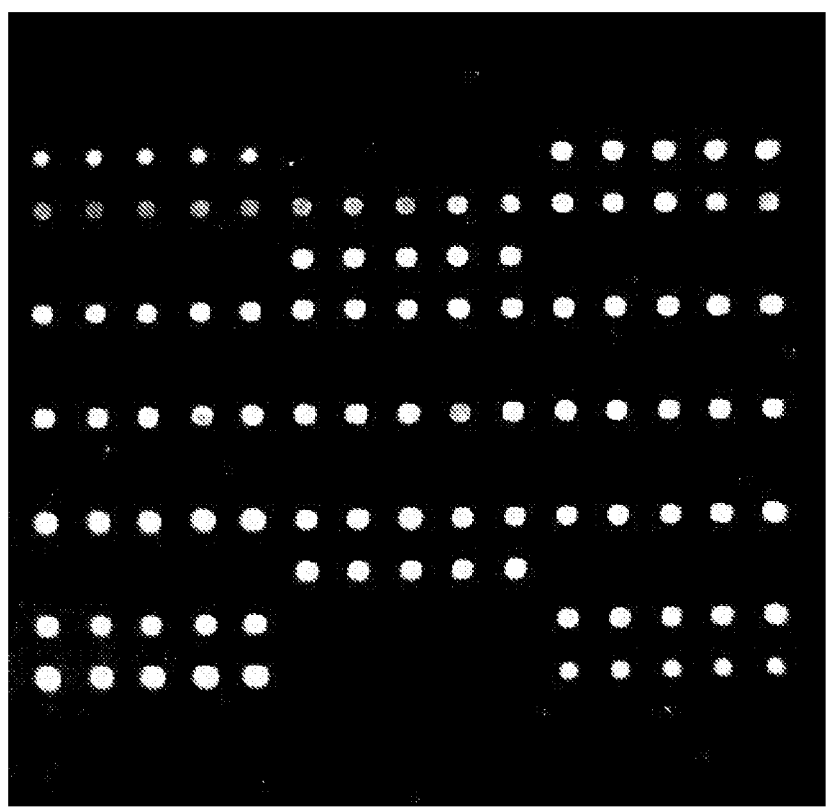
FIGS. 3(a) and 3(b) show the microarray results for PCR products of deafness genes detected using a microfluidic device according to one aspect of the present disclosure.

FIG. 3(*a*) shows the microarray probe arrangement. FIG. 3(*b*) is the fluorescence image of microarray processed according to above described procedures with 2 hours of PCR reaction and 15 min of hybridization. Both the positive control spot and the sample spot showed strong fluorescence signal indicating effective detection.

The invention claimed is:

1. A microfluidic device for integrated target amplification and detection, comprising:
   a microchip comprising:
   at least one sample reservoir;
   at least one amplification chamber, wherein the amplification chamber is configured as a detachable amplification tube;
   at least one connecting structure configured to connect the microchip to the at least one amplification chamber;

at least one reagent reservoir;
at least one mixing reservoir; and
at least one detection chamber,
wherein the at least one sample reservoir is connected to the at least one amplification chamber, which is connected to the at least one mixing reservoir;
wherein the at least one reagent reservoir is connected to the at least one mixing reservoir,
wherein the at least one mixing reservoir is connected to the at least one detection chamber;
and wherein the device further comprises a supporting platform which comprises a metal plate having at least one groove, wherein the detachable amplification tube is enclosed or embedded in the at least one groove.

2. The microfluidic device of claim 1, wherein the at least one amplification chamber is assembled on the microchip through the at least one connecting structure, wherein the at least one connecting structure comprises one or more joints, wherein each joint is selected from a screwed nipple, a sleeve joint, and a casting joint.

3. The microfluidic device of claim 1, wherein the at least one detection chamber is detachable from the microchip.

4. The microfluidic device of claim 1, wherein the at least one sample reservoir comprises a reservoir on the microchip for receiving a sample, and a detachable lid on the sample reservoir.

5. The microfluidic device of claim 4, wherein the detachable lid comprises an air inlet and a hydrophobic air-permeable membrane attached to the inside of the lid to cover the air inlet from the inside.

6. The microfluidic device of claim 1, wherein the at least one sample reservoir is connected to the at least one amplification chamber via a first channel in the microchip, a first joint, or a first elastic tube, or any combination thereof, wherein the first channel comprises a valve that controls the opening or closing of the channel, wherein the first joint is a screwed nipple, a sleeve joint, or a casting joint.

7. The microfluidic device of claim 6, wherein the at least one sample reservoir is connected to the first channel in the microchip, the first channel is connected to the first joint, the first joint is connected to the first elastic tube, and the first elastic tube is connected to the at least one amplification chamber.

8. The microfluidic device of claim 1, wherein the at least one amplification chamber is connected to the at least one mixing reservoir via a second channel in the microchip, a second joint, or a second elastic tube, or any combination thereof, wherein the second channel comprises a valve that controls the opening or closing of the channel, wherein the second joint is a screwed nipple, a sleeve joint, or a casting joint.

9. The microfluidic device of claim 8, wherein the at least one amplification chamber is connected to the second elastic tube, the second elastic tube is connected to the second joint, the second joint is connected to the second channel in the microchip, and the second channel is connected to the at least one mixing reservoir.

10. The microfluidic device of claim 1, wherein the at least one detection chamber is connected to an inlet channel opening via a first inlet channel in the microchip.

11. The microfluidic device of claim 10, wherein the at least one detection chamber is connected to a second inlet channel in the microchip.

12. The microfluidic device of claim 11, wherein the second inlet channel in the microchip is connected to the at least one mixing reservoir via a third channel in the microchip, wherein the third channel comprises a valve that controls the opening or closing of the channel, and wherein the valve is an elastomeric valve, a phase change valve, or a torque valve.

13. The microfluidic device of claim 1, wherein the at least one detection chamber is connected to an outlet channel opening via an outlet channel in the microchip.

14. The microfluidic device of claim 1, wherein the at least one reagent reservoir is connected to the at least one mixing reservoir via a fourth channel in the microchip, wherein the fourth channel comprises a valve that controls the opening or closing of the channel, and wherein the valve is an elastomeric valve, a phase change valve, or a torque valve.

15. The microfluidic device of claim 1, wherein the at least one reagent reservoir comprises a reservoir on the microchip for receiving at least one reagent, and a detachable lid on the reagent reservoir.

16. The microfluidic device of claim 15, wherein the detachable lid comprises an air inlet and a hydrophobic air-permeable membrane attached to the inside of the lid to cover the air inlet from the inside.

17. The microfluidic device of claim 1, wherein the number of the at least one sample reservoir and the number of the at least one amplification chamber are the same.

18. The microfluidic device of claim 1, wherein the at least one detection chamber comprises an array for detection of one target molecule or a plurality of target molecules in a sample.

19. The microfluidic device of claim 18, wherein the array is a microarray, such as a nucleic acid microarray, a protein microarray, a tissue microarray, an antibody microarray, or a combination thereof.

20. The microfluidic device of claim 1, further comprising a control subsystem comprising a fluid control subsystem, an optical subsystem, and/or a thermal control subsystem.

21. The microfluidic device of claim 20, wherein the fluid control subsystem comprises at least one fluid container, at least one pump, and/or at least one valve, and channel(s) that connects or connect the at least one fluid container, at least one pump, and/or at least one valve, and wherein the valve is an elastomeric valve, a phase change valve, or a torque valve.

22. The microfluidic device of claim 21, wherein the at least one fluid container comprises a solution container, a gas container, and/or a waste container.

23. The microfluidic device of claim 20, wherein the fluid control system comprises a pump connected to both the outlet channel opening and the mixing reservoir opening, via a bi-directional valve.

24. The microfluidic device of claim 20, wherein the thermal control subsystem comprises a heating and/or cooling element for the at least one amplification chamber.

25. The microfluidic device of claim 24, wherein the thermal control subsystem further comprises a heating and/or cooling element for the at least one detection chamber.

26. The microfluidic device of claim 20, wherein the optical subsystem comprises a camera for capturing an image indicating a reaction in the detection chamber.

27. The microfluidic device of claim 1, wherein the volume of the at least one mixing reservoir is greater than the total volume of the at least one sample reservoir and the at least one reagent reservoir.

28. The microfluidic device of claim 1, wherein the supporting platform is detachable from the microchip.

29. The microfluidic device for integrated target amplification and detection of claim 1, wherein the amplification tube is cylindrical.

\* \* \* \* \*